(12) United States Patent
Maier et al.

(10) Patent No.: US 11,883,510 B2
(45) Date of Patent: Jan. 30, 2024

(54) DENTAL COMPOSITION COMPRISING A PARTICULATE CARRIER SUPPORTING A COINITIATOR

(71) Applicant: DENTSPLY SIRONA INC., York, PA (US)

(72) Inventors: Maximilian Maier, Osnabrück (DE); Joachim E. Klee, Radolfzell (DE); Christian Scheufler, Engen (DE); Caroline Renn, Singen (DE); Florian Szillat, Constance (DE)

(73) Assignee: DENTSPLY SIRONA INC., York, PA (US)

( * ) Notice: Subject to any disclaimer, the term of this patent is extended or adjusted under 35 U.S.C. 154(b) by 0 days.

(21) Appl. No.: 17/959,768

(22) Filed: Oct. 4, 2022

(65) Prior Publication Data

US 2023/0100120 A1  Mar. 30, 2023

Related U.S. Application Data

(63) Continuation of application No. 16/642,163, filed as application No. PCT/EP2018/073231 on Aug. 29, 2018, now abandoned.

(30) Foreign Application Priority Data

Aug. 31, 2017 (EP) .................... 17188788

(51) Int. Cl.
| | |
|---|---|
| *A61K 6/889* | (2020.01) |
| *A61K 6/30* | (2020.01) |
| *A61K 6/40* | (2020.01) |
| *A61K 6/62* | (2020.01) |
| *A61K 6/17* | (2020.01) |

(52) U.S. Cl.
CPC ............... *A61K 6/889* (2020.01); *A61K 6/17* (2020.01); *A61K 6/30* (2020.01); *A61K 6/40* (2020.01); *A61K 6/62* (2020.01)

(58) Field of Classification Search
CPC .................................. A61K 6/30; A61K 6/889
See application file for complete search history.

(56) References Cited

U.S. PATENT DOCUMENTS

| | | | |
|---|---|---|---|
| 3,534,122 A | 10/1970 | Cornell | |
| 3,655,605 A | 4/1972 | Smith et al. | |
| 3,814,717 A | 6/1974 | Wilson et al. | |
| 4,143,018 A | 3/1979 | Crisp et al. | |
| 4,209,434 A | 6/1980 | Wilson et al. | |
| 4,298,738 A | 11/1981 | Lechtken et al. | |
| 4,324,744 A | 4/1982 | Lechtken et al. | |
| 4,360,605 A | 11/1982 | Schmitt et al. | |
| 4,376,835 A | 3/1983 | Schmitt et al. | |
| 4,385,109 A | 5/1983 | Lechtken et al. | |
| 4,814,362 A | 3/1989 | Billington et al. | |
| 5,154,762 A | 10/1992 | Mitra et al. | |
| 5,318,929 A | 6/1994 | Jana et al. | |
| 5,360,770 A | 11/1994 | Chadwick | |
| 5,501,727 A | 3/1996 | Wang et al. | |
| 6,048,667 A | 4/2000 | Eldin et al. | |
| 2001/0014453 A1 | 8/2001 | McGall et al. | |
| 2004/0079258 A1 | 4/2004 | Hoescheler et al. | |
| 2006/0160919 A1 | 7/2006 | Brugger et al. | |
| 2008/0306182 A1 | 12/2008 | Brugger et al. | |
| 2013/0338252 A1 | 12/2013 | Klee et al. | |
| 2014/0039087 A1 | 2/2014 | Stelzig et al. | |
| 2018/0092811 A1 | 4/2018 | Klee et al. | |
| 2018/0214351 A1 | 8/2018 | Fik et al. | |

FOREIGN PATENT DOCUMENTS

| | | | | |
|---|---|---|---|---|
| EP | 173567 A2 | 3/1986 | | |
| EP | 969789 B1 | 8/2006 | | |
| EP | 1156053 B1 | 12/2006 | | |
| EP | 3124009 A1 | 1/2017 | | |
| EP | 3124477 A1 | 2/2017 | | |
| EP | 2705827 B1 | 12/2017 | | |
| EP | 2859876 B1 | 6/2020 | | |
| JP | 2018172333 A | 12/2021 | | |
| WO | WO-9704361 A1 * | 2/1997 | ............. | G03F 7/031 |
| WO | 9917716 A2 | 4/1999 | | |
| WO | 2012045736 A1 | 4/2012 | | |
| WO | 2014040729 A1 | 3/2014 | | |
| WO | 2014060450 A1 | 4/2014 | | |
| WO | 2016156363 A1 | 10/2016 | | |
| WO | 2017017155 A1 | 2/2017 | | |
| WO | 2017060459 A1 | 4/2017 | | |
| WO | 2009147033 A1 | 12/2019 | | |

OTHER PUBLICATIONS

Schroeder et al (Dental Materials, 24 (2008) 686-693) (Year: 2008).*

* cited by examiner

*Primary Examiner* — Benjamin J Packard
(74) *Attorney, Agent, or Firm* — DENTSPLY SIRONA INC.

(57) ABSTRACT

The present invention relates to a dental composition comprising a photoinitiator system comprising a particulate carrier supporting a coinitiator covalently bonded to the surface of the carrier. Furthermore, the present invention relates to a use of the particulate carrier in a dental composition.

The particulate carrier displays multiple covalently bonded tertiary amino groups and/or tertiary phosphine groups on the surface, for crosslinking monomers, oligomers and/or polymers having one or more polymerizable double bonds.

14 Claims, No Drawings

# DENTAL COMPOSITION COMPRISING A PARTICULATE CARRIER SUPPORTING A COINITIATOR

This is a continuation application of pending U.S. patent application Ser. No. 16/642,163 filed Feb. 26, 2020.

FIELD OF THE INVENTION

The present invention relates to a dental composition comprising a photoinitiator system comprising a particulate carrier supporting a coinitiator covalently bonded to the surface of the carrier. Furthermore, the present invention relates to a use of the particulate carrier in a dental composition.

The particulate carrier displays multiple covalently bonded tertiary amino groups and/or tertiary phosphine groups on the surface, for crosslinking monomers, oligomers and/or polymers having one or more polymerizable double bonds.

BACKGROUND OF THE INVENTION

EP3124477 discloses an aqueous dental composition having a pH of at most 7 which may contain filler particles treated with a coupling agent in order to enhance the bond between the filler and the matrix, whereby coupling agents include gamma-aminopropyltrimethoxysilane. None of the coinitiators of an initiator system essentially present in a dental composition disclosed in EP3124477 is linked to a particulate carrier.

The restoration of teeth commonly involves a light curable dental composition containing free-radically polymerizable resins. Light curing of a dental composition involves a photoinitiator system generating free radicals upon exposure to visible light. Free radicals may be typically produced by either of two pathways:
 (1) the photoinitiator compound undergoes excitation by energy absorption with subsequent decomposition into one or more radicals (Norrish type 1), or
 (2) the photoinitiator compound undergoes excitation and the excited photoinitiator compound interacts with a coinitiator compound by either energy transfer or a redox reaction to form free radicals from any of the compounds (Norrish type II).

In order for a photoinitiator to be useful in a dental composition, the quantum yield indicating the efficiency of the conversion of radiation to radicals needs to be high since absorption or shielding of light by further components of the dental composition limit the amount of energy available for absorption by the photoinitiator. Accordingly, only about 70 percent conversion of the polymerizable groups may be expected in a polymerization of a typical dental composition, whereby the mechanical strength of the polymerized dental composition is less than optimal and unreacted monomers may leach out of the polymerized dental composition. Leaching monomers may have detrimental effects. In order to alleviate this problem, multifunctional monomers are frequently used which are more likely to be included in the polymer network.

In addition, photoinitiators are required to have a high acid resistance, solubility, thermal stability, and storage stability when incorporated into a dental composition.

Finally, given that dental compositions usually contain (meth)acrylate or (meth)acrylamide monomers, free radical photocuring may be inhibited by the presence of oxygen. Oxygen inhibition is due to the rapid reaction of propagating radicals with oxygen molecules to yield peroxyl radicals which are not as reactive towards carbon-carbon unsaturated double bonds and therefore do not initiate or participate in any photopolymerization reaction. Oxygen inhibition may lead to premature chain termination and, therefore, incomplete photocuring. Nevertheless, a certain degree of oxygen inhibition on the top surface of the adhesive layer is required for the bonding to the adjacent restorative.

Accordingly, the polymerization initiator system has a critical influence on the quality of the dental material. Conventionally, camphor quinone optionally in combination with a tertiary amine, or 2, 4, 6-trimethylbenzoylphenyl phosphinate (Irgacure® TPO) are frequently used as photoinitiator system. However, the presence of amines in acrylate-containing compositions can cause yellowing in the resulting photocured composition, create undesirable odours, and soften the cured composition because of chain transfer reactions and therefore, often require the use of stabilizers. Moreover, the use of aromatic amines gives rise to toxicological concerns.

Furthermore, it is desirable that the photoinitiator system can be light-activated at a long wavelength in order to avoid damage of soft tissue during polymerization of the dental composition in the patient's mouth. Accordingly, the photoinitiator system is required to contain a chromophoric group efficiently absorbing light of the desired wavelength in a range of from 400 to 800 nm. However, an increase of the absorption coefficient of the photoinitiator system increases the coloration of the photoinitiator system and thereby the coloration of the dental composition before light curing. Accordingly, it is necessary that the chromophoric groups are efficiently destroyed during polymerization so that the coloration of the initiator system disappears in the polymerized dental composition, the so-called "photobleaching". A destruction of the chromophoric groups during polymerization may also be useful in increasing the depth of cure of the dental composition since activating light is not shielded from unpolymerized layers of the dental composition by the photoinitiator system present in polymerized layers covering the unpolymerized layers.

Typically, for improving the polymerization performance of a photoinitiator system of a dental composition, a coinitiator, e.g. in the form of an organic compound having a tertiary amino group or a tertiary phosphine group, is contained in a dental composition. For example, dental compositions containing a coinitiator in the form of an organic compound having a tertiary amino group are disclosed in WO/2017/017155 and EP 2859876 A2. Dental compositions containing a coinitiator in the form of an organic compound having a tertiary phosphine group are for example disclosed in U.S. Pat. No. 3,534,122 A, WO 2009/147033 A1, WO 2012/045736 A1 and WO 2014/060450 A1.

The coinitiators disclosed in the above cited documents are small organic molecules.

SUMMARY OF THE INVENTION

It is an object of the present invention to provide a dental composition comprising a photoinitiator system comprising a photosensitizer and a particulate carrier supporting a coinitiator covalently bonded to the surface of the carrier, wherein the particulate carrier provides
 no or negligible yellowing upon curing of the dental composition,
 an alleviated leaching problem of the cured dental composition, and
 no or negligible toxicity.`

Moreover, it is the problem of the present invention to provide a use of the particulate carrier in a dental composition.

According to a first aspect, the present invention provides a dental composition comprising
(a) a compound having a polymerizable double bond,
(b) a photoinitiator system comprising
    (b1) a photosensitizer absorbing light in the range of from 400 to 800 nm, and
    (b2) a particulate carrier supporting a coinitiator covalently bonded to the surface of the carrier, wherein the particulate carrier displays multiple covalently bonded tertiary amino groups and/or tertiary phosphine groups on the surface, for crosslinking monomers, oligomers and/or polymers having one or more polymerizable double bonds.

According to a second aspect, the present invention provides a use of the particulate carrier displaying multiple covalently bonded tertiary amino groups and/or tertiary phosphine groups on the surface, in a dental composition for crosslinking polymer chains formed by polymerizing a compound having a polymerizable double bond.

The present invention is based on the recognition that the particulate carrier (b2) provides a cured dental composition which has no yellowing or yellowing is significantly reduced compared with conventional dental compositions exclusively containing non-covalently bonded coinitiator compounds. In addition, the leaching problem of the cured dental composition is alleviated. Besides, the particulate carrier (b2) is harmless or at least has a significantly reduced toxicity compared with conventional, non-covalently bonded coinitiator compounds.

DETAILED DESCRIPTION OF PREFERRED EMBODIMENTS

The term "polymerizable double bond" as used herein in connection with compound (a) means any double bond capable of addition polymerization, in particular free radical polymerization, preferably a carbon-carbon double bond.

The term "photoinitiator system" means any system of one or a mixture of two or more compounds that form free radicals when activated, e.g. by exposure to light and/or interaction with one or more further compounds in a photochemical process, whereby polymerization of polymerizable compounds, such as the compound having a polymerizable double bond (a), is initiated.

The term "photosensitizer" as used herein in connection with the photoinitiator system (b) refers to any chemical compound that forms free radicals when activated, e.g. by exposure to light or interaction with a further compound, such as the coinitiator covalently bonded to the particulate carrier (b2) in a photochemical process.

The term "particulate carrier" refers to any particulate material to which surface a coinitiator having a tertiary amino group or a tertiary phosphine group can be covalently bond, either to the particulate material itself by means of any suitable chemical reaction forming a covalent bond, or by surface treatment of the particulate material with a coating agent to which the coinitiator is non-covalently bonded. Any coating agent is suitable as long as it is suitable for dental compositions. Preferably, the coating agent is an organosilane.

The term "coinitiator" used in connection with the particulate carrier (b2) refers to compounds having a tertiary amino group and/or tertiary phosphine group which interacts with the photosensitizer in the generation of radicals initiating a polymerization reaction.

The present dental composition provides a cured dental composition based on a polymerization of a compound having a polymerizable double bond (a) by free radical polymerization initiated by the photoinitiator system (b).

The present invention relates to a dental composition, which may be used as a dental glass ionomer cement, a dental cement, a dental adhesive composition, a dental bonding agent, a dental primer, a dental infiltrant, a pit and fissure sealant, a dental desensitizing composition, a pulp capping composition, a dental composite, and a sealing and protecting composition for naked tooth necks.

The Compound Having a Polymerizable Double Bond (a)

The dental composition according to the invention comprises (a) a compound having a polymerizable bond, which compound is termed as "compound (a)" hereinafter. The dental composition may comprise one or a mixture of two or more compounds (a).

The term "polymerizable double bond" as used herein in connection with compound (a) means any double bond capable of addition polymerization, in particular free radical polymerization, preferably a carbon-carbon double bond, more preferably alkenyl group(s) and/or vinyl group(s).

Optionally, compound (a) has a carboxylic acid group or hydroxyl group to make the compound (a) water-soluble. The term "water-soluble" used in this connection means that at least 0.1 g, preferably 0.5 g of compound (a) dissolves in 100 g of water at 20° C.

Preferably, compound (a) is hydrolysis-stable. The term "hydrolysis-stable" used in this connection means that the compound (a) is stable to hydrolysis in an acidic medium, such as in a dental composition. In particular, the compound (a) does not contain groups, e.g. as ester groups, which hydrolyse in aqueous media at pH 3 at room temperature within one month.

Preferably, compound (a) is (a1) a water-soluble, hydrolysis-stable monomer having a single polymerizable double bond and optionally a carboxylic acid group or hydroxyl group, which is termed as "monomer (a1)" hereinafter.

More preferably, a water-soluble, hydrolysis-stable monomer having a single polymerizable double bond and a carboxylic acid group is a compound represented by the general formula (IV):

(IV)

In formula (IV), $R^3$ is a hydrogen atom or a straight chain or branched $C_{1-3}$ alkyl group, and $R^4$ is a hydrogen atom or a straight-chain or branched $C_{1-6}$ alkyl group which may be substituted by a —COOH group. In formula (IV), the dotted line indicates that $R^3$ may be in either the cis or trans orientation. Preferably, $R^3$ is a hydrogen atom, and $R^4$ is a hydrogen atom or a $C_{1-3}$ alkyl group optionally substituted with a —COOH group. More preferably, $R^3$ is a hydrogen atom, and $R^4$ is a hydrogen atom or a methyl group substituted with a —COOH group, that is compound of formula (IV) is acrylic acid or itaconic acid. Most preferably, the compound of formula (IV) is acrylic acid.

It is preferred that in formula (IV), residues $R^3$ and $R^4$ are selected with the proviso that the molecular weight of monomer (a1) is at most 200 Da, preferably at most 150 Da, more preferably at most 100 Da.

Monomers (a1) comprising a carboxylic acid group, such as compounds of formula (IV), are particularly advantageous, since carboxylic acid groups can undergo a cement reaction with an optional reactive particulate filler (c) described below, whereby a further improved setting or curing reaction may be attained.

Besides of monomer (a1), compound (a) may be a (meth) acrylate compound which may be selected from the group of methyl acrylate, methyl methacrylate, ethyl acrylate, ethyl methacrylate, propyl acrylate, propyl methacrylate, isopropyl acrylate, isopropyl methacrylate, 2-hydroxyethyl acrylate, 2-hydroxyethyl methacrylate (HEMA), hydroxypropyl acrylate, hydroxypropyl methacrylate, tetrahydrofurfuryl acrylate, tetrahydrofurfuryl methacrylate, glycidyl acrylate, glycidyl methacrylate, the diglycidyl methacrylate of bisphenol A ("bis-GMA"), glycerol mono- and di-acrylate, glycerol mono- and dimethacrylate, ethyleneglycol diacrylate, ethyleneglycol dimethacrylate, polyethyleneglycol diacrylate (where the number of repeating ethylene oxide units vary from 2 to 30), polyethyleneglycol dimethacrylate (where the number of repeating ethylene oxide units vary from 2 to 30 especially triethylene glycol dimethacrylate ("TEGDMA"), neopentyl glycol diacrylate, neopentylglycol dimethacrylate, trimethylolpropane triacrylate, trimethylol propane trimethacrylate, mono-, di-, tri-, and tetra-acrylates and methacrylates of pentaerythritol and dipentaerythritol, 1,3-butanediol diacrylate, 1,3-butanediol dimethacrylate, 1,4-butanedioldiacrylate, 1,4-butanediol dimethacrylate, 1,6-hexane diol diacrylate, 1,6-hexanediol dimethacrylate, di-2-methacryloyloxyethyl hexamethylene dicarbamate, di-2-methacryloyloxyethyl trimethylhexanethylene dicarbamate, di-2-methacryloyl oxyethyl dimethylbenzene dicarbamate, methylene-bis-2-methacryloxyethyl-4-cyclohexyl carbamate, di-2-methacryloxyethyl-dimethylcyclohexane dicarbamate, methylene-bis-2-methacryloxyethyl-4-cyclohexyl carbamate, di-1-methyl-2-methacryloxyethyl-trimethylhexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-metha-cryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl4-cyclohexyl carbamate, 2,2'-bis(4-acryloxyphenyl)propane, 2,2'bis(4-acryloxyphenyl) propane, 2,2'-bis[4(2-hydroxy-3-methacryloxy-phenyl)] propane, 2,2'-bis[4(2-hydroxy-3-acryloxy-phenyl)propane, 2,2'-bis(4-methacryloxyethoxyphenyl)propane, 2,2'-bis(4-acryloxyethoxyphenyl)propane, 2,2'-bis(4-methacryloxypropoxyphenyl)propane, 2,2'-bis(4-acryloxypropoxyphenyl)propane, 2,2'-bis(4-methacryloxydiethoxyphenyl) propane, 2,2'-bis(4-acryloxydiethoxyphenyl)propane, 2,2'-bis[3(4-phenoxy)-2-hydroxypropane-1-methacrylate] propane, and 2,2'-bis[3(4-phenoxy)-2-hydroxypropane-1-acryalte]propane, 2-hydroxyethyl acrylamide (HEAA), N,N-dimethyl(meth)acrylamide, N,N-diethyl(meth)acrylamide, N,N-di-n-propyl(meth)acrylamide, and N-ethyl-N-methyl(meth)acrylamide may be mentioned. Other suitable examples compounds (b) are isopropenyl oxazoline, vinyl azalactone, vinyl pyrrolidone, styrene, divinylbenzene, urethane acrylates or methacrylates, epoxy acrylates or methacrylates and polyol acrylates or methacrylates.

Furthermore, compound (a) may be (a2) a water-soluble, hydrolysis stable polymerizable crosslinker having at least two polymerizable carbon-carbon double bonds (a2) is termed as "crosslinker (a2)" hereinafter.

The term "polymerizable carbon-carbon double bond" as used herein in connection with the crosslinker (a2) means any carbon-carbon double bond capable of addition polymerization, in particular free radical polymerization, preferably alkenyl group(s) and/or vinyl group(s).

Preferably, the crosslinker (a2) is a polymerizable compound of the following formula (V), which is disclosed in EP2705827 and WO2014040729:

wherein
A is a group of the following formula (VI)

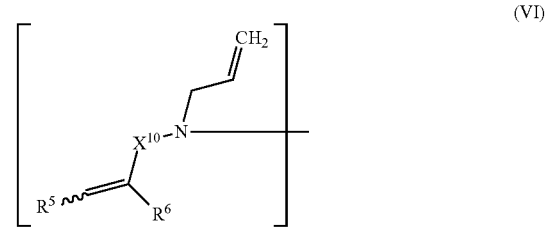

$X^{10}$ is CO, CS, $CH_2$, or a group $[X^{100}Z^{10}]_k$, wherein $X^{100}$ is an oxygen atom, a sulfur atom or NH, $Z^{10}$ is a straight chain or branched $C_{1-4}$ alkylene group, and k is an integer of from 1 to 10;

$R^5$ is a hydrogen atom,
—$COOM^{10}$,
a straight chain or branched $C_{1-16}$ alkyl group which may be substituted by a $C_{3-6}$ cycloalkyl group, a $C_{6-14}$ aryl or $C_{3-14}$ heteroaryl group, —$COOM^{10}$, —$PO_3M^{10}$, —O—$PO_3M^{10}_2$ or —$SO_3M^{10}$,
a $C_{3-6}$ cycloalkyl group which may be substituted by a $C_{1-16}$ alkyl group, a $C_{6-14}$ aryl or $C_{3-14}$ heteroaryl group, —$COOM^{10}$, —$PO_3M^{10}$, —O—$PO_3M^{10}_2$ or —$SO_3M^{10}$,
a $C_{6-14}$ aryl or $C_{3-14}$ heteroaryl group which may be substituted by —$COOM^{10}$, —$PO_3M^{10}$, —O—$PO_3M^{10}_2$ or —$SO_3M^{10}$, $R^6$ is a hydrogen atom,
—$COOM^{10}$
a straight chain or branched $C_{1-16}$ alkyl group which may be substituted by a $C_{6-14}$ aryl or $C_{3-14}$ heteroaryl group, —$COOM^{10}$, —$PO_3M^{10}$, —O—$PO_3M^{10}_2$ and —$SO_3M^{10}$, a $C_{3-6}$ cycloalkyl group which may be substituted by a $C_{1-16}$ alkyl group, a $C_{6-14}$ aryl or $C_{3-14}$ heteroaryl group, —COOM$^{10}$, —PO$_3$M$^{10}$, —O—PO$_3$M$^{10}{}_2$ or —SO$_3$M$^{10}$, or a $C_{6-14}$ aryl or $C_{3-14}$ heteroaryl group which may be substituted by —COOM$^{10}$, —PO$_3$M$^{10}$, —O—PO$_3$M$^{10}{}_2$ and —SO$_3$M$^{10}$, $L^c$ is a single bond or a linker group;

B independently is a group according to the definition of A, a group of the following formula (VII)

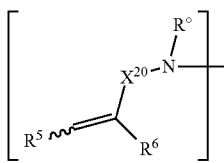

(VII)

wherein $X^{20}$ independently has the same meaning as defined for $X^1$ in formula (VI), $R^5$ and $R^6$ are independent from each other and independently have the same meaning as defined for formula (VI), $R^o$ is a hydrogen atom, a straight chain or branched $C_{1-16}$ alkyl group which may be substituted by a $C_{3-6}$ cycloalkyl group, a $C_{6-14}$ aryl or $C_{3-14}$ heteroaryl group, —COOM$^{10}$, —PO$_3$M$^{10}$, —O—PO$_3$M$^{10}{}_2$ or —SO$_3$M$^{10}$, a $C_{3-6}$ cycloalkyl group which may be substituted by a $C_{1-16}$ alkyl group, a $C_{6-14}$ aryl or $C_{3-14}$ heteroaryl group, —COOM$^{10}$, —PO$_3$M$^{10}$, —O—PO$_3$M$^{10}{}_2$ or —SO$_3$M$^{10}$, a $C_{6-14}$ aryl group which may be substituted by —COOM$^{10}$, —PO$_3$M$^{10}$, —O—PO$_3$M$^{10}{}_2$ or —SO$_3$M$^{10}$, a group of the following formula (VIII)

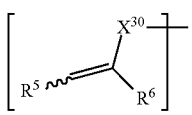

(VIII)

wherein $X^{30}$ is CO, —CH$_2$CO—, CS, or —CH$_2$CS—, $R^5$ and $R^6$ which are independent from each other and independently have the same meaning as defined for formula (VI), or a group $[X^{40}Z^{200}]_p E$, wherein $Z^{200}$ is a straight chain or branched $C_{1-4}$ alkylene group, $X^{40}$ is an oxygen atom, a sulfur atom or NH, E is a hydrogen atom,

PO$_3$M$_2$, a straight chain or branched $C_{1-16}$ alkyl group which may be substituted by a $C_{3-6}$ cycloalkyl group, a $C_{6-14}$ aryl or $C_{3-14}$ heteroaryl group, —COOM$^{10}$, —PO$_3$M$^{10}$, —O—PO$_3$M$^{10}{}_2$ or —SO$_3$M$^{10}$, a $C_{3-6}$ cycloalkyl group which may be substituted by a $C_{1-16}$ alkyl group, a $C_{6-14}$ aryl or $C_{3-14}$ heteroaryl group, —COOM$^{10}$, —PO$_3$M$^{10}$, —O—PO$_3$M$^{10}{}_2$ or —SO$_3$M$^{10}$, a $C_{6-14}$ aryl or $C_{3-14}$ heteroaryl group which may be substituted by —COOM$^{10}$, —PO$_3$M$^{10}$, —O—PO$_3$M$^{10}{}_2$ or —SO$_3$M$^{10}$, and $p^c$ is an integer of from 1 to 10;

and n' is an integer of from 1 to 4;

wherein M$^{10}$ which are independent from each other each represent a hydrogen atom or a metal atom. Preferably, when $L^c$ is a single bond, B cannot be a group according to the definition of A or a group of the formula (VII).

The following groups are preferred groups of formula (VI), wherein M$^{10}$ is a hydrogen atom or a metal atom:

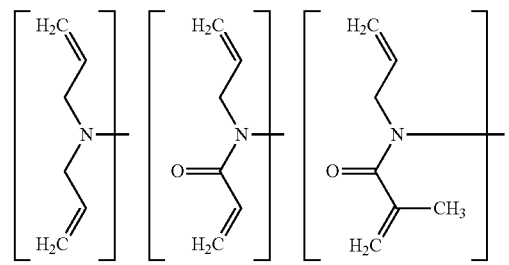

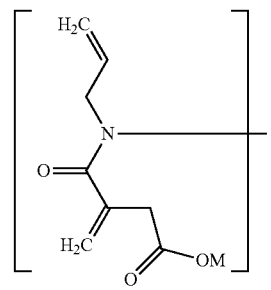

Preferred divalent linker groups may be selected from methylene, ethylene, propylene, butylene and the following divalent groups:

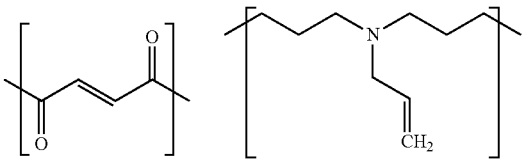

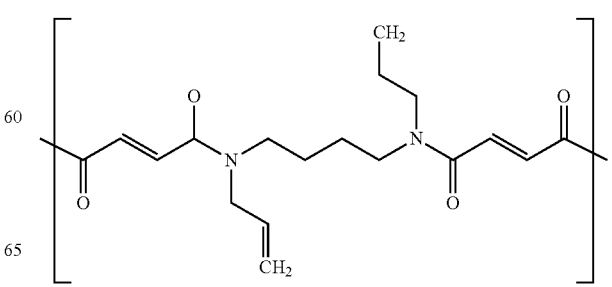

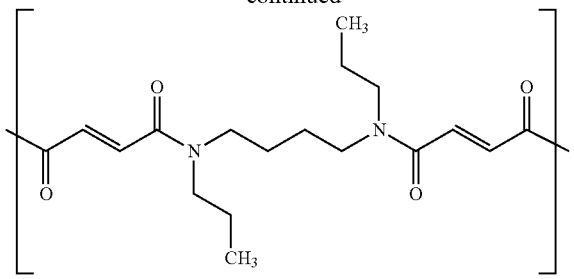

N,N'-(2E)-but-2-en-1,4-diallylbis-[(N-prop-2-en-1) amide and N,N-di(allyl acrylamido) propane are preferred.

Alternatively or additionally, compound (a) may be a crosslinker selected from the group consisting of an alkylenediol dimethylacrylate such as 1,3-butanediol dimethacrylate, 1,4-butanediol dimethacrylate, an alkylenediol divinyl ether such as 1,4-butanediol divinyl ether, di(ethylene glycol) dimethacrylate, di(ethylene glycol) divinyl ether, pentaerythritol diacrylate monostearate, ethylene glycol dimethacrylate, trimetylolpropane trimethacrylate, pentaerythritol triacrylate or triallyl ether, pentaerythritol tetraacrylate and trimetylolpropane triacrylate.

Preferably, compound (a) is contained in the dental composition in an amount of from 0.1 to 20, more preferably 1 to 15 even more preferably 2 to 10 percent by weight based on the total weight of the dental composition. When compound (a) is absent, no light-curing of the dental composition is possible. That is, the dental composition cannot be cured upon irradiation with light. On the other hand, when the amount of compound (a) exceeds 20 percent of weight, shrinkage of the cured dental composition may occur.

The term "photocurable" refers to a dental composition that will polymerize into a crosslinked polymer network when irradiated for example with actinic radiation such as ultraviolet (UV), visible, or infrared radiation. "Actinic radiation" is any electromagnetic radiation that is capable of producing photochemical action and can have a wavelength of at least 150 nm and up to and including 1250 nm, and typically at least 400 nm and up to and including 800 nm.

Compound (a) is preferably selected in view of a good processability and applicability of the final dental composition, in particular in terms of viscosity. Therefore, the viscosity of compound (a) is preferably in the range of 0.1 to 100 mPa·s, more preferably 0.3 to 50 mPa·s, even more preferably 0.5 to 25 mPa·s, yet even more preferably 0.8 to 10 mPa·s, in particular 0.9 to 3 mPa·s.

The Photoinitiator System (b)

The dental composition according to the present invention comprises a photoinitiator system (b) comprising (b1) a photosensitizer absorbing light in the range of from 400 to 800 nm, which is termed as "photosensitizer (b1)" hereinafter. The photoinitiator system (b) may comprise one or a mixture of two or more photosensitizers (b1).

Suitable photosensitizers (b1) for the photosensitizer system (b) are Norrish type I and Norrish type II photosensitizers.

The term "Norrish type I" refers to a photosensitizer undergoing excitation by energy absorption with subsequent decomposition of the compound into one or more radicals.

The term "Norrish type II" refers to a photosensitizer undergoing excitation, and the excited photosensitizer interacts with a second compound, such as a coinitiator, an electron donor, or a sensitizer, by either energy transfer or a redox reaction to form free radicals from any of the compounds.

Suitable Norrish type I photosensitizers are for example phosphine oxides or Si- or Ge-acyl compounds.

Phosphine oxide photosensitizers may have a functional wavelength range of about 380 nm to about 450 nm, which include acyl and bisacyl phosphine oxides such as those described in U.S. Pat. Nos. 4,298,738, 4,324,744 and 4,385,109 and EP 0 173 567. Specific examples of the acylphosphine oxides include 2,4,6-trimethylbenzoyldiphenylphosphine oxide, bis(2,4,6-trimethylbenzoyl)phenylphosphine oxide, dibenzoylphenylphosphine oxide, bis(2,6-dimethoxybenzoyl)phenylphosphine oxide, tris(2,4-dimethylbenzoyl)phosphine oxide, tris(2-methoxybenzoyl)phosphine oxide, 2,6-dimethoxybenzoyldiphenylphosphine oxide, 2,6-dichlorobenzoyldiphenylphosphine oxide, 2,3,5,6-tetramethylbenzoyldiphenylphosphine oxide, benzoyl-bis(2,6-dimethylphenyl)phosphonate, and 2,4,6-trimethylbenzoylethoxyphenylphosphine oxide. Commercially available phosphine oxide photosensitizers capable of free-radical initiation when irradiated at wavelength ranges of greater than about 380 nm to about 450 nm include bis(2,4,6-trimethylbenzoyl)phenyl phosphine oxide (IRGACURE 819), bis(2,6-dimethoxybenzoyl)-(2,4,4-trimethylpentyl) phosphine oxide (CGI 403), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700), a 1:1 mixture, by weight, of bis(2,4,6-trimethylbenzoyl)phenyl phosphine oxide and 2-hydroxy-2-methyl-1-phenylpropane-1-one (DAROCUR 4265), and ethyl 2,4,6-trimethylbenzylphenyl phosphinate (LUCIRIN LR8893X). Typically, the phosphine oxide photosensitizer is present in the composition in catalytically effective amounts, such as from 0.1 percent by weight to 5.0 percent by weight, based on the total weight of the composition.

Suitable Si- or Ge-acyl compounds preferably have the following formula (IX):

wherein
X is a group of the following formula (X):

wherein
M is Si or Ge;
R$^{10}$ represents a substituted or unsubstituted hydrocarbyl or hydrocarbylcarbonyl group;
R$^{11}$ represents a substituted or unsubstituted hydrocarbyl or hydrocarbylcarbonyl group;
R$^{12}$ represents a substituted or unsubstituted hydrocarbyl group; and
R$^9$ i) has the same meaning as X, whereby the compound of formula (IX) may be symmetrical or unsymmetrical; or
ii) is a group of the following formula (XI):

wherein

Y represents a single bond, an oxygen atom or a group NR', wherein R' represents a substituted or unsubstituted hydrocarbyl group;

$R^{13}$ represents a substituted or unsubstituted hydrocarbyl group, a trihydrocarbylsilyl group, a mono(hydrocarbyl-carbonyl)dihydrocarbylsilyl group or a di(hydrocarbyl-carbonyl)monohydrocarbylsilyl group.

It was surprisingly found that Si- or Ge-acyl compounds of formula (IX) represent 1,2-diketone photosensitizers which are particularly suitable for dental compositions. With compounds of formula (IX), a high polymerization efficiency is attained, and no coloration problems occur, or in a polymerization system comprising a conventional photosensitizer such as camphor quinone, coloration is efficiently suppressed. Furthermore, compounds of formula (IX) have a light absorption within the wavelength range typically applied in dental application, they are compatible with the ingredients of dental compositions and besides, they are considered physiologically harmless.

In connection with the Si- or Ge-acyl compound of formula (IX), the term "substituted" as used herein means that $R^{10}$, $R^{11}$, $R^{12}$, $R^{13}$ and R' may be substituted by a substituent selected from the group consisting of halogen atoms, a nitro group, a cyano group, a hydroxy group, an amino group, $C_{1-6}$ alkyl groups, $C_{1-6}$ alkoxy groups and a —$NR^xR^y$ group wherein $R^x$ and $R^y$ independently from each other represent a $C_{1-6}$ alkyl group. Here, illustrative of the halogen atoms can be fluorine, chlorine, bromine and iodine. The $C_{1-6}$ alkyl groups are, for example, methyl, ethyl, n-propyl, isopropyl and n-butyl. Illustrative of the $C_{1-6}$ alkoxy groups are, for example, methoxy, ethoxy and propoxy. The alkyl moieties in these substituents may be linear, branched or cyclic. Preferably, the substituent is selected from a chlorine atom, a nitro group, a $C_{1-4}$ alkoxy group and a —$NR^xR^y$ group wherein $R^x$ and $R^y$ independently from each other represent a $C_{1-4}$ alkyl group.

If $R^{10}$, $R^{11}$ and $R^{12}$ are substituted, then it is preferred that they are substituted with 1 to 3 substituents, more preferably with 1 substituent.

In the compound of formula (IX), moieties $R^{10}$, $R^{11}$ and $R^{12}$ may be defined as follows:

$R^{10}$ and $R^{11}$ independently from each other represent a substituted or unsubstituted hydrocarbyl or hydrocarbylcarbonyl group, and $R^{12}$ represents a substituted or unsubstituted hydrocarbyl group.

The hydrocarbyl group may be an alkyl group, a cycloalkyl group, a cycloalkylalkyl group, an arylalkyl group or an aryl group.

An alkyl group may be straight-chain or branched $C_{1-20}$ alkyl group, typically a $C_{1-8}$ alkyl group. Examples for a $C_{1-6}$ alkyl group can include linear or branched alkyl groups having 1 to 6 carbon atoms, preferably 1 to 4 carbon atoms, for example, methyl, ethyl, n-propyl, isopropyl, n-butyl, isobutyl, sec-butyl, tert-butyl, n-pentyl, isopentyl and n-hexyl.

A cycloalkyl group may be a $C_{3-20}$ cycloalkyl group, typically a $C_{3-8}$ cycloalkyl group. Examples of the cycloalkyl group can include those having 3 to 6 carbon atoms, for example, cyclopropyl, cyclobutyl, cyclopentyl and cyclohexyl.

A cycloalkylalkyl group may have 4 to 20 carbon atoms and may include a combination of a linear or branched alkyl group having 1 to 6 carbon atoms and a cycloalkyl group having 3 to 14 carbon atoms. Examples of the cycloalkylalkyl(–) group can for example, include methylcyclopropyl(–) methylcyclobutyl(–), methylcyclopentyl(–), methylcyclohexyl(–), ethylcyclopropyl(–), ethylcyclobutyl(–), ethylcyclopentyl(–), ethylcyclohexyl(–), propylcyclopropyl(–), propylcyclobutyl(–), propylcyclopentyl(–), propylcyclohexyl(–).

An arylalkyl(–) group may be a $C_{7-20}$ arylalkyl(–) group, typically a combination of a linear or branched alkyl group having 1 to 6 carbon atoms and an aryl(–) group having 6 to 10 carbon atoms. Specific examples of an arylalkyl(–) group are a benzyl(–) group or a phenylethyl(–) group.

An aryl group can include aryl groups having 6 to 10 carbon atoms. Examples of the aryl group are phenyl and naphtyl.

The hydrocarbylcarbonyl groups of $R^{10}$ and $R^{11}$ represent acyl groups ($R_{org}$—(C=O)—) in which the organic residue $R_{org}$ is a hydrocarbyl residue as defined above.

Compound of formula (IX) may contain one or two hydrocarbylcarbonyl groups, that is either one of $R^{10}$ or $R^{11}$ is a hydrocarbylcarbonyl group, or both $R^{10}$ and $R^{11}$ are hydrocarbylcarbonyl groups. Preferably, compound of formula (V) contains one hydrocarbylcarbonyl group.

Preferably, the hydrocarbylcarbonyl group is an arylcarbonyl group, more preferably a benzoyl group.

Preferably, $R^{10}$ and $R^{11}$ are independently selected from the group consisting of a straight chain or branched $C_{1-6}$ alkyl group, and a phenyl or benzoyl group which may optionally be substituted by one to three substitutents selected from halogen atoms, a nitro group, a $C_{1-4}$ alkoxy group and a —$NR^xR^y$ group wherein $R^x$ and $R^y$ independently from each other represent a $C_{1-4}$ alkyl group, and $R^{12}$ is a straight chain or branched $C_{1-6}$ alkyl group or a phenyl group.

Most preferably, $R^{10}$ and $R^{11}$ are independently selected from the group consisting of a straight chain or branched $C_{1-4}$ alkyl group, and a phenyl or benzoyl group which may optionally be substituted with one substituent selected from the group consisting of selected from a halogen atom, a nitro group, a $C_{1-4}$ alkoxy group and a —$NR^xR^y$ group wherein $R^x$ and $R^y$ independently from each other represent a $C_{1-4}$ alkyl group, and $R^{12}$ is a straight chain or branched $C_{1-4}$ alkyl group.

In the compound of formula (IX), $R^9$ may have the same meaning as X, whereby the compound of formula (IX) may be symmetrical or unsymmetrical. Alternatively, $R^9$ may represent a substituted or unsubstituted hydrocarbyl group, or a group of formula (XI). Preferably, if $R^9$ has the same meaning as X, then compound of formula (IX) is unsymmetrical. If $R^9$ represents a substituted or unsubstituted hydrocarbyl group, then the hydrocarbyl group has the same meaning as defined above for $R^{10}$ and is independently selected therefrom.

In the group of formula (XI) of compound of formula (IX), $R^{13}$ represents a substituted or unsubstituted hydrocarbyl group, a trihydrocarbylsilyl group, a mono(hydrocarbylcarbonyl)-dihydrocarbylsilyl group or a di(hydrocarbylcarbonyl)monohydrocarbylsilyl group.

If $R^{13}$ of formula (XI) is a trihydrocarbylsilylgroup, a mono(hydrocarbylcarbonyl)-dihydrocarbylsilyl group or a di(hydrocarbylcarbonyl)monohydrocarbylsilyl group, each of the hydrocarbyl and hydrocarbylcarbonyl groups has the same meaning as defined for $R^{10}$, $R^{11}$ and $R^{12}$ and is independently selected therefrom.

In formula (XI), R' has the same meaning as defined for $R^{12}$ and is independently selected therefrom.

For example, compounds of formula (IX) wherein $R^9$ has the same meaning as X and which are symmetrical may be have the following structural formulae:

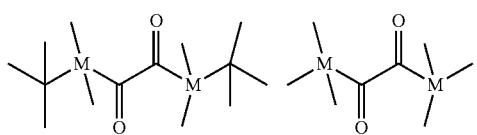

For example, compounds of formula (IX) wherein $R^9$ represents a group of formula (XI) wherein Y is a bond, an oxygen atom or a NR' group, and $R^{13}$ represents a substituted or unsubstituted hydrocarbyl group may have the following structural formulae:

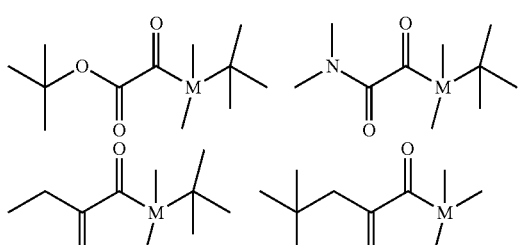

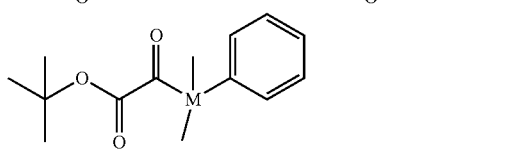

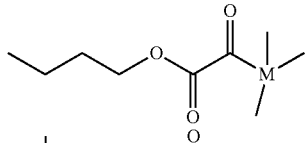

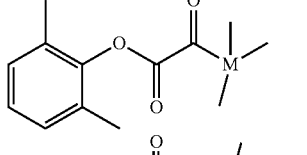

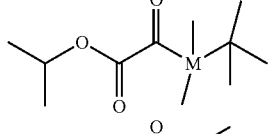

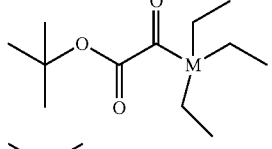

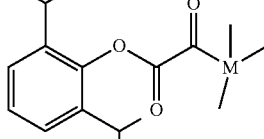

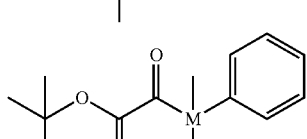

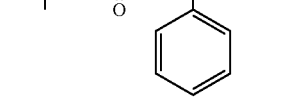

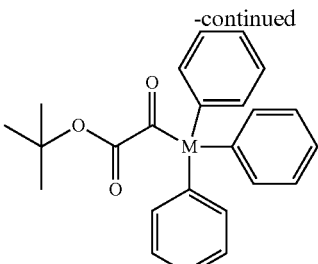

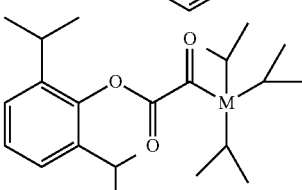

For example, compounds of formula (IX) wherein $R^9$ represents a group of formula (XI) wherein $R^{13}$ represents a trihydrocarbylsilyl group have the following structural formulae:

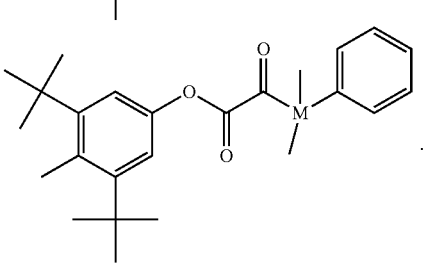

Preferably, compound of formula (IX) is selected from the group consisting of:

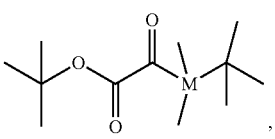

wherein compounds of formula (IX) with M=Si are particularly preferred.

More preferably, compound of formula (IX) has the following structural formula:

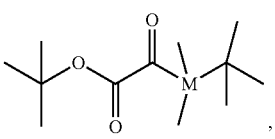

wherein it is particularly preferred that M=Si. That is, tert-butyl (tert-butyldimethylsilyl)-glyoxylate) (DKSi) is particularly preferred.

In case the dental composition is in the form of an acidic composition, that is a composition having a pH of less than 7, depending on the composition's pH level, it is preferred to select compounds of formula (IX) with the proviso that they do not contain ester groups, or at least only ester groups which do not significantly hydrolyse in aqueous media at pH 3 at room temperature within one month. Thereby, an advantageous stability of an acidic dental composition, that is a composition having a pH of less than 7, in terms of shelf-life stability of the uncured dental composition as well as stability after curing in the mouth of a patient is ensured. Therefore, for acidic dental compositions, particularly preferred are compounds of formula (IX) excluding $R^9$ being a group of formula (XI) in which Y is an oxygen atom.

Furthermore, since the acylsilyl moiety (—C(=O)—Si—) might be sensitive to basic conditions, that is a pH higher than 7, it is preferred to suitably select a pH value of the composition being higher than 7 with the proviso that the acylsilyl moiety is not cleaved in aqueous media at the selected basic pH at room temperature within one month.

The compound of the formula (IX) may be a known compound which is commercially available or a may be prepared according to published procedures, as described for example in WO 2017/060459 A1.

Suitable Norrish type II photosensitizers may be selected from the group consisting of camphorquinone, benzil, 2,2'-3 3'- and 4,4'-dihydroxylbenzil, 2,3-butanedione, 2,3-pentanedione, 2,3-hexanedione, 3,4-hexanedione, 2,3-heptanedione, 3,4-heptanedione, 2,3-octanedione, 4,5-octanedionefuril, biacetyl, 1,2-cyclohexanedione, 1,2-naphthaquinone, and acenaphthaquinone. Camphorquinone is preferred.

Preferably, irrespective whether Norrish type I or II, the photosensitizer (b1) is a 1,2-diketone, even more preferably camphor quinone or a Si- or Ge-acyl compound of formula (IX), yet even more preferably camphor quinone or DKSi, and most preferably camphor quinone.

Besides of the photosensitizer (b1), the photoinitiator system (b) further comprises (b2) a particulate carrier supporting a coinitiator covalently bonded to the surface of the carrier, which is termed as "particulate carrier (b2)" hereinafter. The photoinitiator system (b) may comprise one or a mixture of two or more particulate carriers (b2).

The particulate carrier (b2) supports a coinitiator covalently bonded to the surface of the carrier, wherein the particulate carrier displays multiple covalently bonded tertiary amino groups and/or tertiary phosphine groups on the surface, for crosslinking monomers, oligomers and/or polymers having one or more polymerizable double bonds.

It was surprisingly found that the particulate carrier (b2) provides for a cured dental composition which has no yellowing or yellowing is significantly reduced compared with conventional dental composition having exclusively non-covalently bonded coinitiator compounds. Furthermore, the leaching problem of the cured dental composition is alleviated. Finally, the particulate carrier (b2) is harmless or at least has a significantly reduced toxicity compared with non-covalently bonded coinitiator compounds.

Preferably, the covalently bonded tertiary amino groups and/or tertiary phosphine groups are selected from moieties of the following formulae (I) and (II):

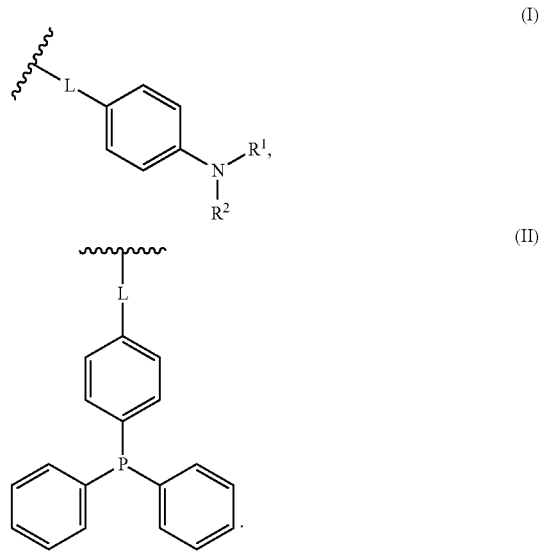

In formula (I), $R^1$ and $R^2$, which may be the same or different, independently represent a $C_{1-6}$ straight-chain, $C_{3-6}$ branched or cyclic alkyl group. In formulae (I) and (II), L is a single bond or a divalent linker group.

Preferably, in formula (I), $R^1$ and $R^2$, which may be the same or different, independently represent a $C_{1-4}$ straight-chain or branched alkyl group, more preferably a C1 or C2 straight-chain alkyl group, most preferably a methyl group.

For L, the divalent linker group may be a hydrocarbon group which may be aliphatic and/or aromatic, preferably aliphatic, and preferably has 1 to 45 carbon atoms. The aliphatic hydrocarbon group may be saturated or unsaturated. The hydrocarbon group may be substituted with 1 to 6 $C_{1-4}$ alkyl groups. Specific examples of the alkyl groups are methyl, ethyl, n-propyl, i-propyl, n-butyl, i-butyl or tert.-butyl. In a preferred embodiment, for L, the hydrocarbon group of the linker group may contain 1 to 20 heteroatoms selected from oxygen, nitrogen and sulphur. The oxygen atoms, nitrogen atoms and sulphur atoms in the hydrocarbon group may be in the form of ether or thioether bonds, amine bonds, keto or sulfoxide groups, carboxylic acid or ester groups, amide groups, sulfonic acid or ester groups, hydroxyl groups and thiol or thioester groups.

Preferably, the divalent linker group is a divalent $C_{1-20}$ hydrocarbon which may contain one or more heteroatoms selected from the group of an oxygen atom, a sulfur atom, and a nitrogen atom. More preferably, the divalent linker group is an aliphatic group in the form of a linear $C_1$ to $C_{20}$ or branched $C_3$ to $C_{20}$ alkylene group, linear $C_2$ to $C_{20}$ and branched $C_3$ to $C_{20}$ alkenylene group, $C_3$ to $C_{20}$ cycloalkylene or cycloalkenylene group which may contain 1 to 20 heteroatoms selected from oxygen, nitrogen and sulphur, which heteroatoms may be in the form described above.

According to one aspect of the invention, the divalent linker group is a group of the following formula (III):

In formula (III), a is 0 or an integer of from 1 to 10, and Het is selected from the group of sulfur, oxygen, and a nitrogen atom substituted with a hydrogen atom or a straight-chain $C_{1-6}$ alkyl group or a branched or cyclic $C_{3-6}$ alkyl group.

According to another aspect of the invention, the divalent linker group may be an alkylene(polyoxyalkylene) group. The alkylene(polyoxyalkylene) for the divalent linker group is not particularly limited, but preferably, it is a $C_{2-6}$alkenylene-(O—$C_{2-6}$ alkylene) wherein k is 1 to 20. Preferably, the alkylene(polyoxyalkylene) is ethylene(polyoxyethylene) wherein k is 1 to 10, most preferably 1 to 5.

Most preferably, in formulae (I) and (II), L is a single bond.

The moieties of formulae (I) and (II) may be covalently bonded to the surface of the particulate carrier via any covalent bond formed by an organic reaction, preferably a carboxylic acid ester bond, a carboxylic acid amide bond, a sulfonamide bond, an oxo- or thio-ether bond, a carbamate bond, a thiocarbamate bond or an urea bond, more preferably a carboxylic acid ester bond and a carboxylic acid amide bond, most preferably a carboxylic acid amide bond.

Preferably, the particulate carrier is selected from a microparticle, a nanoparticle and a polycondensate.

The term "microparticle" means a particle having an average particle size within the micrometer range, preferably up to 250 µm, more preferably 0.05 to 125 µm, and most preferably 1 to 50 µm.

The term "nanoparticle" means a particle having an average particle size within the micrometer range, preferably up to 250 nm, more preferably 0.05 to 125 nm, and most preferably 1 to 50 nm.

The term "average particle size" refers to the arithmetic mean diameter of a particle and may be determined by any suitable means, such as transmission or high resolution scanning electron microscopy. The average particle size may be determined as so-called "D50" value, which is the particle size corresponding to the volume basis cumulative 50% size.

The above described microparticle or nanoparticle may for example be composite particles comprising two or more components, for example at least one particulate inorganic component such as a particulate metal oxide and at least one organic component such as a surface treatment agent, e.g. a silane treatment agent. The microparticle or nanoparticle may also be a particle essentially consisting of one component, e.g. of a polycondensate of organic compounds such as organoalkoxysilanes.

The term "polycondensate" as used in connection with the particulate carrier (b2) means any particulate product having polycondensation reaction products. Polycondensation products are obtained by a polymerization reaction in which molecules join together whereby small compounds such as water or an alcohol leave the molecules. For example, the polycondensate may be any suitable organic polycondensation reaction product, preferably a polycondensation reaction product of organoalkoxysilanes.

The particulate carrier (b2) in the form of a nanoparticle preferably has a density of covalently bonded tertiary amino groups and/or tertiary phosphine group of from 0.1 to 100 groups per $nm^2$.

It is preferred that the particulate carrier is a microparticle or nanoparticle comprising silica, alumina, zirconia, titania, or a mixture thereof.

According to a particularly preferred embodiment, the nanoparticle is a polycondensate obtainable by a process comprising the following three steps (i) to (iii):

(i) hydrolysing a mixture containing
  (A) a silica precursor component, and optionally
  (B) one or more compounds selected from compounds of aluminum, zinc, titanium, zirconium, tungsten, ytterbium, hafnium, bismuth, barium, strontium, silver, tantalum, lanthanum, tin, boron, and cerium;
(ii) converting the silica precursor component (A) and the optionally compounds (B) into a particulate oxide having an average particle size of from 1 to 50 nm;
(iii) treating the particulate oxide with a silane treatment agent having one or more covalently bonded tertiary amino groups or tertiary phosphine groups for obtaining a polycondensate displaying multiple covalently bonded tertiary amino groups or tertiary phosphine groups on the surface.

In step (i), the silica precursor component (A) is preferably silicon alkoxide $Si(OR^7)_4$, wherein $R^7$ is a linear $C_{1-8}$ or branched or cyclic Cm alkyl group, preferably a linear or branched $C_{1-4}$ alkyl group, most preferably a linear $C_1$ or $C_2$ alkyl group. The optional compound (B) is preferably a metal alkoxide $M(OR^8)_n$, wherein $R^8$ has the same meaning as $R^7$ of the silicon alkoxide, M is selected from the group consisting of aluminum, zinc, titanium, zirconium, tungsten, ytterbium, hafnium, bismuth, barium, strontium, silver, tantalum, lanthanum, tin, boron, and cerium, and n is an integer of 1 to 4 corresponding to the oxidation state of the selected M. Preferably M is aluminum, titanium, zirconium or zirconium.

The hydrolysing in step (i) is effected by adding water to the silica precursor component (A) and the optional compound (B), whereby the corresponding hydroxide is formed from silica precursor component (A) and optional compound(s) (B), and as a byproduct, an alcohol is formed.

In step (ii), converting is a polycondensation reaction in which from the hydroxide obtained in step (i), a particulate oxide is formed as polycondensate of the silica precursor component (A) and the optional compound(s) (B), and water is formed as a byproduct. The polycondensation reaction is preferably carried out in a mixture of water and an alcohol, for example ethanol or methanol.

Preferably, step (i) and (ii) independently from each other are base or acid catalyzed. Base catalyzation may preferably be carried out by setting the pH within a range of more than 7 to 14, more preferably 9 to 13, most preferably 11 to 12. For base catalyzation, any suitable basic compound may be used for setting the pH, for example with ammonia. Acid catalyzation may preferably be carried out by setting the pH within a range of 0 to less than 7, more preferably 1 to 6, most preferably 2 to 5. For acid catalyzation, any suitable acidic compound may be used for setting the pH, for example hydrochloric acid, sulfuric acid and phosphoric acid.

The reaction mixture of step (ii) provides a colloidal metal oxide, which is typically aged for obtaining a gel thereof. Aging means that the reaction mix is allowed to stand for a predetermined period of time at a predetermined temperature. For example, aging may be carried out for 0.5 to 6 h, preferably at a temperature of 15 to 35° C.

After aging, the resulting gel is typically dried and calcined for obtaining a particulate oxide. Drying is carried out to remove water and alcohol. Therefore, the temperature for drying is suitably selected in view of the alcohol present in the reaction mixture and in view of the pressure applied. For example, for a reaction mixture of step (ii) containing water and ethanol, drying at standard pressure (100 kPa) may be carried out at a temperature of 100° C. or more. Calcination is carried out to remove organic species and to convert byproducts formed due to incomplete reactions in steps (i) and (ii), for example silanols, to the desired particulate oxide. Preferably, calcination is carried out at 400 to 1000° C., more preferably 500 to 800° C., most preferably 550 to 650° C.

The combination of steps (i) and (ii) is well known as sol-gel process in the field of chemistry and described in general for example in Ullmann's Encyclopedia of Industrial Chemistry, vol. A. 14, page 248 to 250, $5^{th}$ edition, 1989, VCH Verlagsgesellschaft mbH. Specifically, silica sol-gel processes for preparing nanoparticles are described in I. A. Rahman et al., "Synthesis of Silica Nanoparticles by Sol-Gel: Size-Dependent Properties, Surface Modification, and Applications in Silica-Polymer Nanocomposites—A Review", Journal of Nanomaterials Volume 2012, Article ID 132424, Hindawi Publishing Corporation.

Preferably, in step (iii), the silane treatment agent has one or more covalently bonded tertiary amino groups and/or tertiary phosphine groups selected from the moieties of the formulae (I) and (II) described above.

One preferred silane treatment agent for step (iii) is an organosilane of formula (XII)

$(R_A,R_B,R_C)Si(R_H)_n$ (XII)

are applied, wherein n is 1 to 3 and the number of substituents $R_C$, $R_B$, $R_C$ is 4-n.

Preferably, n is 2 or 3, more preferably 3.

In formula (XII), $R_A$, $R_B$, $R_C$, which may be the same or different, represent an unreactive group or a polymerizable group, and at least one of $R_A$, $R_B$, $R_C$ is substituted with a covalently bonded tertiary amino group and/or tertiary phosphine group. Unreactive groups for $R_A$, $R_B$ and $R_C$ may be represented by alkyl groups, preferably linear $C_{1-8}$ or branched or cyclic $C_{3-8}$ alkyl groups. Polymerizable groups for $R_A$, $R_B$ and $R_C$ are preferably selected from the group consisting of a (meth)acryl group, a vinyl group or an oxirane group, more preferably (meth)acryl group or a vinyl group, and most preferably a (meth)acryl group which may be in the form of e.g. methacryloxy or methacryloxyalkyl wherein alkyl means a linear $C_{1-8}$ or branched or cyclic $C_{3-8}$ alkyl group. Preferably, at least one of $R_A$, $R_B$ and $R_C$ is a polymerizable group.

$R_H$, which may be the same or different if two or three groups $R_H$ are present, represent(s) a hydrolysable group capable of reacting with the surface of the filler material to be coated. $R_H$ may be selected from the group consisting of alkoxy groups, ester groups, halogen atoms and amino group, wherein the alkoxy groups are preferably linear $C_{1-8}$ or branched or cyclic Cm alkoxy groups, and the ester groups are preferably carboxylates having linear $C_{1-8}$ or branched or cyclic $C_{3-8}$ alkyl groups. Most preferably, the hydrolysable group $R_H$ represents an alkoxy group.

Alternatively or additionally to the organosilane of formula (XII), a dipodal organosilane of formula (XIII)

$((R_H)_nSi—R_D)_2CH—R_A$ (XIII)

may be applied. In formula (XIII), $R_A$ and $R_H$ have the same meaning as defined above for the organosilane of formula (XII), $R_D$ represents an alkylene group, and n is 1 to 3, preferably 2 or 3, more preferably 3. Preferably, $R_D$ represents a linear $C_{1-8}$ or branched or cyclic $C_{3-8}$ alkylene group, more preferably a linear or branched $C_{1-4}$ alkylene group.

At least one of $R_A$, $R_B$, $R_C$ of formula (XII) and $R_A$ of formula (XIII) is substituted with a tertiary amino or tertiary phosphine group, which group is preferably selected from the moieties of formulae (XII) and (XIII) described above.

$R_A$, $R_B$, $R_C$ may be substituted with the tertiary amino or tertiary phosphine group via any covalent bond formed by an organic reaction, preferably a carboxylic acid ester bond, a carboxylic acid amide bond, a sulfonamide bond, an oxo- or thio-ether bond, a carbamate bond, a thiocarbamate bond or an urea bond, more preferably a carboxylic acid ester bond and a carboxylic acid amide bond, most preferably a carboxylic acid amide bond.

For example, organosilanes of formula (XII) or (XIII) with $R_H$ being an alkoxy group may be prepared analogous to the synthesis disclosed in EP 1 156 053 A2, which describes how an organic moiety having for example a tertiary amino group can be introduced into a trialkoxysilane. The synthesis starts from an trialkoxysilane having an aminoalkyl, an isocyanatoalkyl or an thiolalkyl group. The trialkoxysilane is reacted with a compound having a tertiary amino group in the form of a maleimide group and a reactive group in the form of a hydroxyl or isocyanate group. The reactive group is reacted with the amino, isocyanate or thiol group of the trialkoxysilane. Thereby, the tertiary amino group is covalently bonded to the trialkoxysilane via a carbamate, thiocarbamate or urea bond.

Alternatively, organosilanes of formula (XII) or (XIII) with $R_H$ being an alkoxy group may for example be prepared analogous to the synthesis disclosed in WO 00/121967 A1 by reacting a trialkoxylsilane having an aminoalkyl group with a compound having an organic moiety and a reactive group in the form of an acyl halogenide (preferably iodide, chloride, bromide, most preferably chloride), whereby the organic group is covalently bonded to the trialkoxysilane via an amide bond.

For example, an organosilane of formula (XII) in which $R_H$ is an alkoxy group and one of $R_A$, $R_B$, $R_C$ is substituted with a tertiary amino group covalently bonded by a carboxylic acid amide group may be prepared starting from a commercially readily available aminoalkyl trialkoxysilane such as (3-aminopropyl)trimethoxysilane (CAS-No. 13822-56-5), which is reacted with an acyl halogenide (preferably iodide, chloride, bromide, most preferably chloride) compound having the moiety of formula (I) or (II).

In addition to the preferred organosilanes of formulae (XII) and (XIII), in step (iii), conventional organosilanes, that is organosilanes without a covalently bonded tertiary amino group and/or tertiary phosphine group may be applied. Particularly preferred conventional organosilanes are for example 3-methacryloxy trimethoxysilane, vinyl-trichlorosilane, tris (2-methoxyethoxy)-vinylsilane or tris (acetoxy)-vinylsilane, or any one of the specific group of organosilanes disclosed in EP 0969789 A1, namely 3-methacryloxypropyltrimethoxysilane, 3-methacryloxypropyldimethoxy-monochlorosilane, 3-methacryloxypropyldichloromonomethoxysilane, methacryloxypropyltri-chlorosilane, 3-methacryloxypropyldichloromonomethyl-silane and 3-methacryloxypropylmonochlorodimethylsilane.

Besides of the photosensitizer (b1) and the particulate carrier (b2), the photoinitiator system (b) may comprise further components, such as an electron donor component, a coinitiator component which is not covalently bonded to any component of the dental composition, and a sensitizer component.

Preferred electron donor components include, for example, amides, ethers, thioethers, ureas, thioureas, ferrocene, sulfinic acids and their salts, salts of ferrocyanide, ascorbic acid and its salts, dithiocarbamic acid and its salts, salts of xanthates, salts of ethylene diamine tetraacetic acid and salts of tetraphenylboronic acid or an organic hydride of Si, Ge or Sn.

More preferably, the electron donor component is an organic hydride compound of Si, Ge or Sn.

Preferred organic hydrides of Si, Ge or Sn have the following formula (XIV):

$$L^*-H \quad (XIV),$$

wherein $L^*$ is a moiety of the following formula (XV)

$$R^a R^b R^c X^*- \quad (XV).$$

In formula (XV), $X^*$ represents Si, Ge, or Sn, $R^a$ represents a hydrogen atom, an organic moiety or a different moiety $L^*$, and $R^b$ and $R^c$, which are independent from each other, represent an organic moiety.

The organic metal hydride of formula (XIV) may react as a hydrogen donating agent in a photoexcitation complex with the alpha-diketone sensitizer. Accordingly, when an alpha-diketone absorbs visible light and forms an exciplex with the organic metal hydride of formula (XIV), a hydrogen transfer may take place from the organic metal hydride to the alpha-diketone compound, whereby the organic metal hydride of formula (XIV) is transformed into a radical specifies capable of facilitating the polymerization reaction.

In formula (XV), $X^*$ represents Si, Ge, or Sn. Preferably, $X^*$ represents Si or Ge. More preferably, $X^*$ is Ge. According to a specific embodiment, compound of formula (XIV) is a silane compound. According to a further specific embodiment, compound of formula (XIV) is a germane compound.

In formula (XV), $R^a$ may be a hydrogen atom, an organic moiety or a different moiety L. When $R^a$ is a hydrogen atom, then the compound of formula (XIV) contains two metal hydride bonds ($X^*$—H). In case $R^a$ is a hydrogen atom, the $X^*$ is Si.

When $R^a$ is an organic moiety, $R^a$ is preferably an aromatic, an aliphatic or an alicyclic group. An aromatic group may be a phenyl group. The phenyl group may be substituted by one or more straight chain or branched alkyl groups having 1 to 6 carbon atoms, alicyclic groups having 3 to 6 carbon atoms, halogen atoms, hydroxyl groups, or amino groups. The aliphatic group may be a straight chain or branched alkyl groups having 1 to 6 carbon atoms which may be substituted by one or more aromatic groups, alicyclic groups having 3 to 6 carbon atoms, halogen atoms, hydroxyl groups or amino groups. An alicyclic group may be a group having 3 to 6 carbon atoms which may be substituted by one or more aromatic groups, aliphatic groups, halogen atoms, hydroxyl groups or amino groups.

When $R^a$ is a different moiety $L^*$, the compound of formula (XIV) of the formula (XIV) contains a metal-metal bond. In case two moieties $L^*$ are present, then each $X^*$, $R^a$, $R^b$ and $R^c$ may be the same or different and independently has the meaning as defined by the present invention.

$R^b$ and $R^c$ which are independent from each other, represent an organic moiety. An organic group may be an aromatic, an aliphatic or an alicyclic group. An aromatic group may be a phenyl group. The phenyl group may be substituted by one or more straight chain or branched alkyl groups having 1 to 6 carbon atoms, alicyclic groups having 3 to 6 carbon atoms, halogen atoms, hydroxyl groups, or amino groups. The aliphatic group may be a straight chain or branched alkyl groups having 1 to 6 carbon atoms which may be substituted by one or more aromatic groups, alicyclic groups having 3 to 6 carbon atoms, halogen atoms, hydroxyl groups or amino groups. An alicyclic group may be a group having 3 to 6 carbon atoms which may be substituted by one or more aromatic groups, aliphatic groups, halogen atoms, hydroxyl groups or amino groups.

According to a preferred embodiment, $R^a$, $R^b$, and $R^c$ in the compound of formula (XIV) are the same and represent an aliphatic, an aromatic or an alicyclic hydrocarbon group.

According to a preferred embodiment, the compound of formula (XIV) is a compound of the following formula:

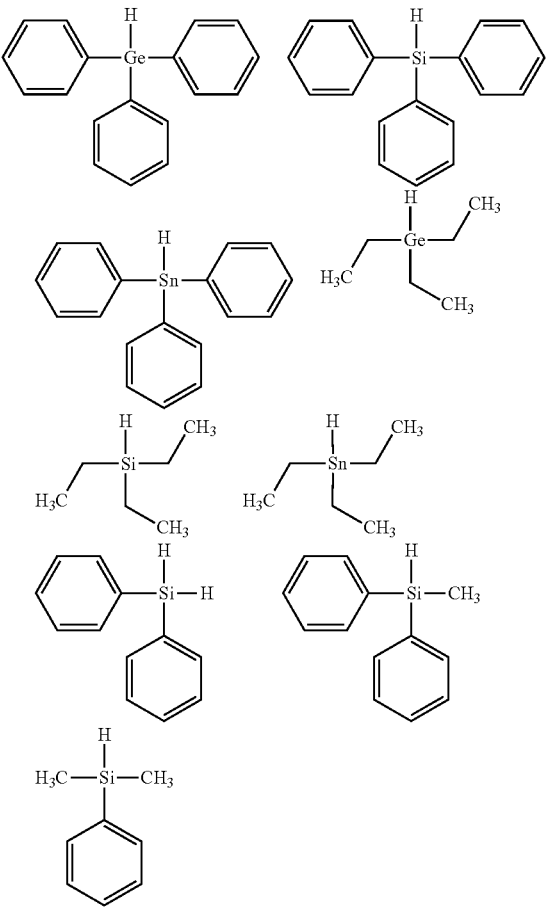

According to a preferred embodiment, the dental composition contains the compound of formula (XIV) in an amount from 0.05 to 5 percent by weight based on the total weight of the composition.

Coinitiator components are preferably selected from iodonium salts, sulfonium salts, phosphonium salts, amine compounds and tertiary aromatic phosphine compounds.

Preferred iodonium, sulfonium or phosphonium salts respectively have a cation selected from:

(1) an iodonium ion of the following formula (XVI):

$$R^{15}-I^+-R^{16} \quad (XVI)$$

wherein
$R^{15}$ and $R^{16}$ which are independent from each other represent an organic moiety;

(2) a sulfonium ion of the following formula (XVII):

$$R^{17}R^{18}R^{19}S^+ \quad (XVII)$$

wherein
$R^{17}$, $R^{18}$ and $R^{19}$ which are independent from each other, represent an organic moiety, and optionally any two of $R^5$, $R^6$ and $R^7$ form a cyclic structure together with the sulfur atom to which they are bound;

(3) a phosphonium ion of the following formula (XVIII):

$$R^{20}R^{21}R^{22}P^+ \quad (XVIII)$$

wherein $R^{20}$, $R^{21}$ and $R^{22}$ which are independent from each other, represent an organic moiety.

Salts having a cation selected from formulae (XVI), (XVII) and (XVIII) represent particularly efficient iodonium, sulfonium or phosphonium salts and significantly improve the polymerization performance of the photoinitiator system.

Preferably, $R^{15}$ and $R^{16}$ of the iodonium ion of formula (XVI), $R^{17}$, $R^{18}$ and $R^{19}$ of the sulfonium ion of (XVII), and $R^{20}$, $R^{21}$ and $R^{22}$ of the phosphonium ion of formula (XVIII) are respectively selected from an aromatic, an aliphatic or an alicyclic group. An aromatic group may be a phenyl group. The phenyl group may be substituted by one or more straight chain or branched alkyl groups having 1 to 6 carbon atoms, straight chain or branched alkoxy groups having 1 to 6 carbon atoms, aromatic groups such as aryl groups or aryloxy groups, alicyclic groups having 3 to 6 carbon atoms, halogen atoms, hydroxyl groups, or amino groups. The aliphatic group may be a straight chain or branched alkyl groups having 1 to 6 carbon atoms which may be substituted by one or more aromatic groups, alicyclic groups having 3 to 6 carbon atoms, halogen atoms, hydroxyl groups or amino groups. An alicyclic group may be a group having 3 to 6 carbon atoms which may be substituted by one or more aromatic groups, aliphatic groups, halogen atoms, hydroxyl groups or amino groups.

More preferably, $R^{15}$ and $R^{16}$ of the iodonium ion of formula (XVI) and $R^{17}$, $R^{18}$ and $R^{19}$ of the sulfonium ion of (XVII) are respectively selected from a phenyl group which may be substituted with 1 to 3 substituents selected from halogen atoms, a cyano group, a hydroxy group, an amino group, $C_{1-6}$ alkyl groups and $C_{1-6}$ alkoxy groups.

According to a preferred embodiment, the iodonium ion of formula (XVI) is a diaryl iodonium ion. Examples of useful diaryl iodonium ions include (4-methylphenyl)[4-(2-methylpropyl) phenyl] iodonium, diphenyliodonium tetrafluoroborate, di(4-methylphenyl)iodonium, phenyl-4-methylphenyliodonium, di(4-heptylphenyl)iodonium, di(3-nitrophenyl)iodonium, di(4-chlorophenyl)iodonium, di(naphthyl)iodonium, di(4-trifluoromethylphenyl)iodonium, diphenyliodonium, di(4-methylphenyl)iodonium; diphenyliodonium, di(4-phenoxyphenyl)iodonium, phenyl-2-thienyliodonium, 3,5-dimethylpyrazolyl-4-phenyliodonium, diphenyliodonium, 2,2'-diphenyliodonium, di(2,4-dichlorophenyl)iodonium, di(4-bromophenyl)iodonium, di(4-methoxyphenyl)iodonium, di(3-carboxyphenyl)iodonium, di(3-methoxycarbonylphenyl)iodonium, di(3-methoxysulfonylphenyl)iodonium, di(4-acetamidophenyl)iodonium, di(2-benzothienyl)iodonium, and diphenyliodonium.

More preferably aromatic iodonium ions of formula (XVI) are selected from the group consisting of diaryliodonium, (4-methylphenyl)[4-(2-methylpropyl) phenyl] iodonium, 4-octyloxyphenyl phenyliodonium, and 4-(1-methylethyl)phenyl 4-methylphenyliodonium. Most preferably, the aromatic iodonium ion of formula (XVI) is diphenyliodonium or (4-methylphenyl)[4-(2-methylpropyl)phenyl]iodonium.

A preferred sulfonium ion of formula (XVII) is S-(phenyl) thianthrenium of the following formula:

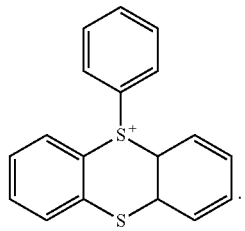

Preferably, in a phosphonium ion of formula (XVIII), $R^{20}$, $R^{21}$ and $R^{22}$ independently from each other represent an aliphatic group, more preferably a straight chain or branched alkyl group having 1 to 6 carbon atoms which may be substituted by one or more aromatic groups, alicyclic groups having 3 to 6 carbon atoms, halogen atoms, hydroxyl groups or amino groups. More preferably, in a phosphonium ion of formula (XVIII), $R^{20}$, $R^{21}$ and $R^{22}$ independently from each other represent a straight chain or branched alkyl group having 1 to 4 carbon atoms which may be substituted by one or more halogen atoms, hydroxyl groups or amino groups.

A particularly preferred phosphonium ion of formula (XVIII) is tetrakis-(hydroxymethyl)-phosphonium (THP).

In the iodonium, sulfonium or phosphonium salts having a cation of formula (XVI), (XVII) or (XVIII), the anion may be selected from hexafluoroantimonate, trifluoromethylsulfate, hexafluorophosphate, tetrafluoroborate, hexafluoroarsenate, and tetraphenylborate.

Preferred amine compounds are tertiary amine compounds, more preferably tertiary amine compounds selected from the group consisting of triethanolamine, 4-N,N-dimethylaminobenzonitrile, methyl N,N-dimethylaminobenzoate, ethyl N,N-dimethylaminobenzoate, N,N-dimethylaminoethyl methacrylate and isoamyl 4-N,N-dimethylaminobenzoate, N,N-dimethylaniline, N,N-dimethyltoluidine, N,N-diethanoltoluidine, dimethylaminoanisole, 1 or 2-dimethylaminonaphthalene. Most preferably, the tertiary amine compound is selected from the group consisting of triethanolamine, methyl 4-N,N-dimethylaminobenzoate, ethyl 4-N,N-dimethylaminobenzoate, 4-N,N-dimethylaminoethyl methacrylate and isoamyl 4-N,N-dimethylaminobenzoate.

Preferred aromatic tertiary phosphine compounds have the following formula (XIX):

$$Z^P—R^P \quad (XIX)$$

wherein
$Z^P$ is a group of the following formula (XX)

$$R^*(Ar^P)P— \quad (XX)$$

wherein
R* represents a substituted or unsubstituted hydrocarbyl group;
$Ar^P$ represents a substituted or unsubstituted aryl or heteroaryl group;
$R^P$ is an aryl group, which may be substituted by one or more groups selected from a hydroxyl group, an amino group, a —$NR^aR^b$ group (wherein $R^a$ and $R^b$, which may be the same or different, are selected from $C_{1-6}$ alkyl groups), a carboxyl group, and a group having a polymerizable double bond;
wherein the group R* and $Ar^P$ may be substituted by one or more groups selected from a hydroxyl group, an oxo group, a —$NR_aR_b$ group (wherein $R_a$ and $R_b$, which may be the same or different, are selected from a hydrogen atom and $C_{1-6}$ alkyl groups), a carboxyl group, and a group having a polymerizable double bond, and $L^P$ may be substituted by one or more groups selected from a hydroxyl group, an oxo group, a —$NR_aR_b$ group (wherein $R_a$ and $R_b$, which may be the same or different, are selected from a hydrogen atom and $C_{1-6}$alkyl groups), a carboxyl group, and a group having a polymerizable double bond.

In formula (XIX), for R*, the monovalent hydrocarbyl group may be an alkyl group, a cycloalkyl group, a cycloalkylalkyl group, an arylalkyl group or an aryl group.

$Ar^P$ represents a substituted or unsubstituted aryl or heteroaryl group. An aryl group may be selected from a phenyl group, a naphtyl group, a tolyl group, a xylyl group, and a styryl group. A heteroaryl group may be a pyridyl group.

$L^P$ is a substituted or unsubstituted divalent hydrocarbyl group which may contain a linkage selected from an ether linkage, a thioether linkage, an ester linkage, an amide linkage, and a urethane linkage. For $L^P$, the divalent hydrocarbyl group may be an alkyldiyl group, a cycloalkyldiyl group, a cycloalkylalkyl-diyl group, an arylalkyl-diyl group or an aryldiyl group. In a cycloalkylalkyl-diyl, one valency may be bonded to each of the cycloalkyl moiety or the alkyl moiety, or both valencies may be bonded to either the cycloalkyl moiety or the alkyl moiety. In a arylalkyl-diyl group, each of the aryl moiety or the alkyl moiety may be monovalent respectively, or either the aryl moiety or the alkyl moiety is divalent, while the other moiety is nonvalent. In a cycloalkylalkyl-diyl, each of the cycloalkyl moiety or the alkyl moiety may be monovalent respectively, or either the cycloalkyl moiety or the alkyl moiety is divalent, while the other moiety is nonvalent.

The following definitions apply both for the monovalent and the divalent hydrocarbyl group, therefore, for the definition of the divalent hydrocarbyl group, the suffixes "diyl" and "-diyl" are bracketed.

An alkyl(diyl) group may be straight-chain or branched $C_{1-20}$ alkyl(diyl) group, typically a $C_{1-8}$ alkyl(diyl) group. Examples for a $C_{1-6}$ alkyl(diyl) group can include linear or branched alkyl(diyl) groups having 1 to 6 carbon atoms, preferably 1 to 4 carbon atoms, for example, methyl(diyl), ethyl(diyl), n-propyl(diyl), isopropyl(diyl), n-butyl(diyl), isobutyl(diyl), sec-butyl(diyl), tert-butyl(diyl), n-pentyl (diyl), isopentyl(diyl) and n-hexyl(diyl).

A cycloalkyl(diyl) group may be a $C_{3-20}$ cycloalkyl(diyl) group. Examples of the cycloalkyl(diyl) group can include those having 3 to 14 carbon atoms, for example, cyclopropyl(diyl), cyclobutyl(diyl), cyclopentyl(diyl) and cyclohexyl(diyl). A cycloalkylalkyl(diyl) group can include those having 4 to 20 carbon atoms.

A cycloalkylalkyl(-diyl) group can include a combination of a linear or branched alkyl(diyl) group having 1 to 6 carbon atoms and a cycloalkyl(diyl) group having 3 to 14 carbon atoms. Examples of the cycloalkylalkyl(-diyl) group can for example, include methylcyclopropyl(-diyl) methylcyclobutyl(-diyl), methylcyclopentyl(-diyl), methylcyclohexyl(-diyl), ethylcyclopropyl(-diyl), ethylcyclobutyl(-diyl), ethylcyclopentyl(-diyl), ethylcyclohexyl(-diyl), propylcyclopropyl(-diyl), propylcyclobutyl(-diyl), propylcyclopentyl(-diyl), propylcyclohexyl(-diyl).

An arylalkyl(-diyl) group may be a $C_{7-20}$ arylalkyl(-diyl) group, typically a combination of a linear or branched alkyl(diyl) group having 1 to 6 carbon atoms and an aryl(-diyl) group having 6 to 10 carbon atoms. Specific examples of an arylalkyl(-diyl) group are a benzyl(-diyl) group or a phenylethyl(-diyl) group.

An aryl(diyl) group can include aryl(diyl) groups having 6 to 10 carbon atoms. Examples of the aryl(diyl) group are phenyl(diyl) and naphtyl(diyl). Aryl(diyl) groups may contain 1 to 3 substituents. Examples of such substituents can include halogen atoms, a cyano group, a hydroxy group, an amino group, $C_{1-6}$ alkyl groups and $C_{1-6}$ alkoxy groups. Here, illustrative of the halogen atoms can be fluorine, chlorine, bromine and iodine. The $C_{1-4}$ alkyl(diyl) groups are, for example, methyl(diyl), ethyl(diyl), n-propyl(diyl), isopropyl(diyl) and n-butyl(diyl). Illustrative of the $C_{1-4}$ alkoxy(diyl) groups are, for example, methoxy(diyl), ethoxy (diyl) and propoxy(diyl). The alkyl(diyl) moieties in these substituents may be linear, branched or cyclic.

Preferably, the hydrocarbyl group is an aryl(diyl) group selected from a phenyl(diyl) group and a naphthyl(diyl) group, which groups may optionally be substituted by one to three groups selected from halogen atoms, a cyano group, an amino group, a hydroxy group, $C_{1-6}$ alkyl groups and C1-6 alkoxy groups, or wherein the hydrocarbyl group is a non-aromatic hydrocarbyl group selected from a straight chain or branched alkyl group, a straight chain or branched alkenyl group, or a straight chain or branched alkynyl group.

The $C_{1-8}$ alkyl(diyl) group and the $C_{3-14}$ cycloalkyl(diyl) group may optionally be substituted by one or more members of the group selected from a $C_{1-4}$ alkyl group, $C_{1-4}$ alkoxy group, a phenyl group, and a hydroxy group. Examples for a $C_{1-4}$ alkyl group can include linear or branched alkyl groups having 1 to 4 carbon atoms, for example, methyl, ethyl, n-propyl, isopropyl, n-butyl, isobutyl, sec-butyl, tert-butyl. Examples for an $C_{1-4}$ alkoxy group can include linear or branched alkoxy groups having 1 to 4 carbon atoms, for example, methoxy, ethoxy, n-propoxy, isopropoxy, n-butoxy, isobutoxy, sec-butoxy, and tert-butoxy.

Moreover, in formula (XIX), any of the hydrocarbyl group may be substituted by one or more groups selected from halogen atoms, a cyano group, an amino group or a hydroxy group. Accordingly, in the hydrocarbyl groups some or all hydrogen atoms are replaced by halogen atoms (e.g., fluoro, bromo, chloro), for example, halo-substituted alkyl groups such as chloromethyl, chloropropyl, bromoethyl and trifluoropropyl, and cyanoethyl.

In case the hydrocarbyl group contains an alkyl(diyl) chain, one or more carbon atoms in the alkyl(diyl) chain may be replaced by an oxygen atom, a sulfur atom, an amide group, an ester group, or a urethane group. In case the hydrocarbyl group is an alkyl group having more than one carbon atom, the alkyl group contains an alkylene. Accordingly, in case the hydrocarbyl group is an n-hexyl group, any of the carbon atoms of the alkylene chain excluding the terminal methyl group may be replaced by an oxygen atom, a sulfur atom, an amide group, an ester group, a urethane group or an NH group. Therefore, the following groups may be given as specific examples in case of one or more oxygen atoms:

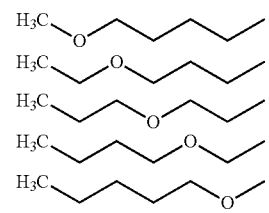

-continued

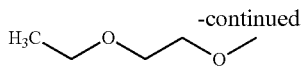

In formula (XIX), group R* and/or $Ar^P$ as well as $R^P$ and/or may be substituted with a polymerizable double bond, preferably a carbon-carbon double bond. Examples of polymerizable carbon-carbon double bonds include vinyl, conjugated vinyl, allyl, acryl, methacryl and styryl. Preferably, the polymerizable double bond is selected from the group consisting of methacryl, acryl and styryl. More preferably, the double bond is styryl.

Preferably, R* and $Ar^P$ independently are aromatic hydrocarbyl groups selected from a phenyl group, a naphtyl group, a tolyl group, a xylyl group, and a styryl group.

As regards $R^P$, this moiety is an aryl group, which may be substituted by one or more groups selected from a hydroxyl group, an amino group, a —$NR_aR_b$ group (wherein $R_a$ and $R_b$, which may be the same or different, are selected from $C_{1-6}$ alkyl groups), a carboxyl group, and a group having a polymerizable double bond. According to a preferred embodiment, $R^P$ is an aryl group substituted by one or more groups selected from a hydroxyl group, an amino group, a —$NR_aR_b$ group (wherein $R_a$ and $R_b$, which may be the same or different, are selected from $C_{1-6}$ alkyl groups), a carboxyl group, and a group having a polymerizable double bond. More preferably, $R^P$ is a phenyl group substituted by one or two groups selected from a hydroxyl group, an amino group, a —$NR_aR_b$ group (wherein $R_a$ and $R_b$, which may be the same or different, are selected from $C_{1-6}$ alkyl groups), a carboxyl group, and a group having a polymerizable double bond.

Even more preferably, the aromatic phosphine compound is a compound of formula (XIX) wherein $Z^P$ is a group of the following formula:

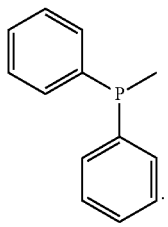

Specific examples for a compound of formula (XIX) include triphenyl phosphine (TPP), 4-(diphenylphosphino) styrene (DPPS), 4-(diphenylphosphino)benzoic acid, 4-(diphenylphosphino) benzoic acid, 3-(diphenylphophonino) propionic acid, (4-(diphenylphosphino) N,N'-dimethylaniline, 2,2'-bis(diphenylphosphino)benzophenone (BDPPEP), bis[2-(di-phenylphosphino)phenyl]ether (BDPPE), (4-Hydroxyphenyl)diphenylphosphine, allyldiphenylphosphine. Preferably, the compound of formula (XIX) is triphenyl phosphine (TPP) or 4-(diphenylphosphino)styrene (DPPS), more preferably 4-(diphenylphosphino)styrene (DPPS).

From the above listed aromatic tertiary compounds of formula (XIX), 4-(diphenylphos-phino)styrene (DPPS) is particularly preferred, since this compound provides for particularly improved photo-bleaching results compared to the already advantageous results obtained with triphenyl phosphine (TPP).

A compound of the formula (XIX) may be a known compound which is commercially available or may be prepared according to published procedures, as described for example in WO/2016/156363 A1.

Furthermore, the photoinitiator system may comprise a sensitizer component selected from a Norrish type I or II sensitizer as described above. The sensitizer component represents an additional photosensitizer other than the photosensitizer (b1) of the photoinitiator system (b).

The Reactive Particulate Filler (c)

Optionally, the dental composition according to the present invention comprises (c) a reactive particulate filler. The dental composition may comprise one or a mixture of two or more reactive particulate fillers (c).

Any granular component being reactive with a polyacidic polymer in a cement reaction may be used as the reactive particulate filler (c), that is, any alkaline granular compound suitable for a dental composition.

The term "cement reaction" as used herein means an acid-base reaction between the reactive particulate filler (c) and a polyacidic polymer in the presence of water. Water provides a medium needed for the ionic acid-base reaction to take place between the reactive particulate filler (c) and a polyacidic polymer.

Preferably, the reactive particulate filler (c) is one or a mixture of two or more metal oxides, most preferably a glass, i.e. an amorphous solid mixture of metal oxides.

The reactive particulate filler (c) in the form of a glass is obtainable by transforming a solid mixture of metal oxides by a thermal melt process into a glass followed by milling, which glass is capable of reacting with a polyacidic polymer in a cement reaction Any conventional reactive dental glass may be used as reactive particulate filler (c). Specific examples of particulate reactive glasses are selected from calcium alumino silicate glass, calcium alumino fluorosilicate glass, calcium aluminumfluoroborosilicate glass, strontium aluminosilicate glass, strontium aluminofluorosilicate glass, strontium aluminofluoroborosilicate glass, or ion-leachable glasses, e.g. as described in U.S. Pat. Nos. 3,655,605, 3,814,717, 4,143,018, 4,209,434, 4,360,605 and 4,376,835.

Alternatively or additionally, reactive metal oxides such as zinc oxide and/or magnesium oxide may be used in glass and/or crystalline form as reactive particulate filler (c).

Preferably, the reactive particulate filler (c) is a glass comprising:
1) 20 to 45% by weight of silica,
2) 20 to 40% by weight of alumina,
3) 20 to 40% by weight of strontium oxide,
4) 1 to 10% by weight of $P_2O_5$, and
5) 3 to 25% by weight of fluoride.

The present dental composition preferably comprises 20 to 90 percent by weight of the reactive particulate filler (c), more preferably 30 to 85 percent by weight, most preferably 20 to 80 percent by weight based on the total weight of the composition.

The reactive particulate filler (c) usually has an average particle size of from 0.1 to 100 μm, preferably of from 1 to 40 μm as measured, for example, by electron microscopy or by using a conventional laser diffraction particle sizing method as embodied by a MALVERN Mastersizer S or MALVERN Mastersizer 2000 apparatus.

The reactive particulate filler (c) may have a unimodal or multimodal (e.g., bimodal) particle size distribution, wherein a multimodal reactive particulate filler (c) represents a mixture of two or more particulate fractions having different average particle sizes.

The reactive particulate filler (c) may be an agglomerated reactive particulate filler which is obtainable by agglomerating a reactive particulate filler in the presence of a modified polyacid and/or polymerizable resin such as (meth) acryloyl monomers. The particle size of the agglomerated reactive particulate filler (c) may be adjusted by suitable size-reduction processes such as milling.

The reactive particulate filler (c) may be surface modified by a surface modifying agent. Preferably, the surface modifying agent is a silane. A silane provides a suitable hydrophobicity to the reactive particulate filler (c), which allows for an advantageous, homogeneous admixture with organic components of the dental composition. The reactive particulate filler (c) may have silane coupling agent(s) on its surface, for example in the form of a coating at least partly, and preferably fully covering the surface of the reactive particulate filler (c).

The Polyacidic Polymer (d)

Optionally, the dental composition according to the present invention comprises (d) a polyacidic polymer which is reactive with the reactive particulate filler in a cement reaction, which is termed as "polyacidic polymer (d)" hereinafter. The dental composition may comprise one or a mixture of two or more polyacidic polymers (d).

Preferably, in the polyacidic polymer (d), the plurality of acidic groups comprises acidic groups selected from a group $(C=Het_1)-Het_2H$, wherein $Het_1$ is an oxygen atom or a sulfur atom, and $Het_2$ is an oxygen atom or a sulfur atom. That is, the acidic groups are preferably selected from carboxylic acid group ($(C=O)-OH$), $(C=S)-SH$, $(C=O)-SH$ and $(C=S)-OH$. The most preferred acidic group is the carboxylic acid group ($(C=O)-OH$).

The acidic groups of the polyacidic polymer (d) can react with the reactive particulate filler (a) to form a glass ionomer cement which can be used as a dental material.

Preferably, the polyacidic polymer (d) is water-soluble. The term "water-soluble" means that at least 0.1 g, preferably 0.5 g of the polyacidic polymer (d) dissolves in 100 g of water at 20° C.

Furthermore, it is preferred that the polyacidic polymer (d) is hydrolysis-stable. "Hydrolysis-stable" means that the polyacidic polymer (d) is stable to hydrolysis in an acidic medium, such as in a dental composition. Specifically, the polyacidic polymer (d) preferably does not contain groups such as ester groups which hydrolyze in aqueous media at pH 3 at room temperature within one month.

In general, the polyacidic polymer (d) may for example be prepared based by polymerizing acrylic acid or a mixture comprising acrylic acid and one or a mixture of polymerizable monomers having a polymerizable double bond and optionally a carboxylic acid group.

According to a particularly preferred embodiment, the polyacidic polymer (d) has repeating units of the following formula (XXI)

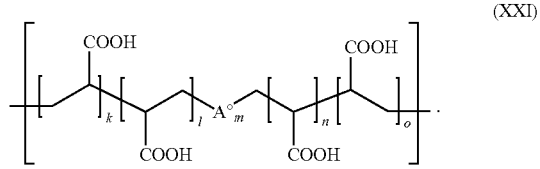
(XXI)

In formula (XXI), $A^\circ$, which may be the same or different, independently is selected from a group of the following formulae (XXIa) to (XXIf):

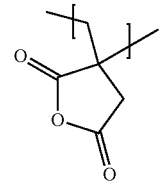
(XXIa)

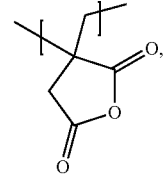
(XXIb)

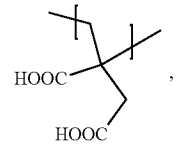
(XXIc)

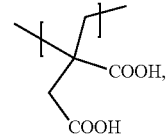
(XXId)

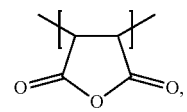
(XXIe)

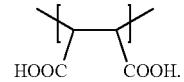
(XXIf)

Furthermore, in formula (XXI), k, l, m, n and o are independently integers of at least 0, k+l+m+n+o is at least 2, and at least one of k, l, n, and o is at least 1.

Preferably, the polyacidic polymer (d) having repeating units of the following formula (XXI) has a weight average molecular weight of 1 to 300 kDa, more preferably 5 to 250 kDa, most preferably 10 to 200 kDa.

The polyacidic polymer (d) having repeating units of the following formula (XXI) may be prepared based by polymerizing acrylic acid or a mixture comprising acrylic acid.

A mixture comprising acrylic acid may further comprise one or more unsaturated monocarboxylic acids or unsaturated dicarboxylic acids or an anhydride of the unsaturated dicarboxylic acids. Specific examples include itaconic acid, maleic acid, methacrylic acid, 2-chloroacrylic acid, 2-cyanoacrylic acid, aconitic acid, mesaconic acid, fumaric acid, glutaconic acid, citraconic acid, utraconic acid, and an anhydride of the unsaturated dicarboxylic acids. Itaconic acid and maleic acid are preferred.

Furthermore, a mixture comprising acrylic acid may further comprise copolymerizable monomers which do not have a carboxylic acid functionality or an anhydride thereof, whereby it is preferable that the proportion of the unsaturated carboxylic acid units is 50% by mol or more of the entire structural units. Preferably, the polyacidic polymer (d) having repeating units of the following formula (XXI) contains from 50 to 100 mole percent of acrylic acid repeating units.

The copolymerizable monomer is preferably an ethylenically unsaturated polymerizable monomer, and the copolymerizable monomer includes, for example, styrene, acrylamide, acrylonitrile, methyl methacrylate, vinyl chloride, allyl chloride, vinyl acetate, 1,1,6-trimethylhexamethylene dimethacrylate ester.

Among the polyacidic polymers (d) having repeating units of the following formula (XXI), homopolymers of acrylic acid and copolymers of acrylic acid and itaconic acid anhydride are preferred. According to a preferred embodiment, the polyacidic polymers (d) having repeating units of the following formula (XXI) is polyacrylic acid or a copolymer of acrylic acid and itaconic anhydride.

Alternatively or additionally to the polyacidic polymer (d) having repeating units of the following formula (XXI), a polyacidic polymer (d) may be used having repeating units of the following formula (XXII)

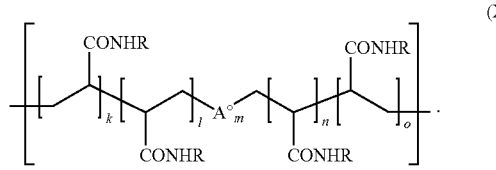

(XXII)

In formula (XXII), R is an organic group having one or more polymerizable double bond, and $A^\circ$ as well as k, l, m, n and o are defined as above for formula (XXI).

Preferably, the polyacidic polymer (d) having repeating units of the following formula (XXII) is prepared by a process in which the polyacidic polymer having repeating units of following formula (XXI) as defined above is reacted with one or more polymerizable compounds of the following formula (XXIII) in a solvent:

R—X°          (XXIII).

In formula (XXIII), $X^\circ$ is selected from an amino group and an isocyanato group, and R is an organic group having one or more polymerizable double bond, for preparing a polymerizable linear polyacidic acrylic polymer having polymerizable pendant groups linked to the acrylic polymer backbone by amide groups. Preferably, $X^\circ$ is an amino group.

The reacting with polymerizable compounds of formula (XXIII) serves to introduce one or more polymerizable moieties into the polyacidic polymer having repeating units of the following formula (XXI), which moieties can be post-polymerized to provide additional covalent crosslinking, imparting additional strength to a cured dental composition comprising the polymer.

According to the present invention, it is not required that the carboxylic acid groups of the polymer are protected. Therefore, the polymerizable polyacidic polymer (d) having repeating units of the following formula (XXII) having polymerizable pendant groups linked to the acrylic polymer backbone by amide groups can be used as a polymer according to the present invention without further treatment.

In an alternative embodiment, the carboxylic acid groups of the polymer are protected. Any protective group for carboxylic acid groups known in the art of organic chemistry may be used, as described e.g. in P. G. M. Wuts and T. W. Greene, Greene's Protective Groups in Organic Synthesis, 4th Edition, John Wiley and Sons Inc., 2007. However, the carboxylic acid groups would have to be deprotected before the polymer may be used in a cement reaction. Therefore, the alternative embodiment is less preferred.

According to a preferred embodiment, $R^\circ$ in formula (XXIII) is a moiety of the following formula (XXIV):

(XXIV)

In formula (XXIV), $R^{23}$ represents a hydrogen atom, a carboxylic acid group or a $C_{1-3}$ alkyl group, $R^{24}$ represents a hydrogen atom, a carboxylic acid group or a $C_{1-3}$ alkyl group, and $L^\circ$ represents a divalent organic linker group.

In formula (XXIV), $L^\circ$ is preferably a group —$Y^\circ L'$-, wherein $Y^\circ$ represents O or NH, and L' represents a divalent organic group.

Preferably, a polymerizable compound of formula (XXIII) with X being an amino group is reacted with the polyacidic polymer having repeating units of formula (XXI) in which the carboxylic acid groups are activated with a coupling agent prior to the reaction with the polymerizable compounds of the formula (XXIII). According to a preferred embodiment, the coupling agent is a carbodiimide. Specifically, the carbodiimide may be selected from N,N'-dicyclohexylcarbodiimide (DCC), N-(3-Dimethylaminopropyl)-N'-ethylcarbonate (EDC), and N,N'-diisopropylcarbodiimide (DIC).

In formula (XXIII), when X is an isocyanato group, addition of a carboxylic acid to the isocyanate initially yields the mixed acid anhydride, decarboxylation of which leads to the N-substituted amide.

In the process for preparing polyacidic polymer having repeating units of formula (XXII), preferably 0.02 to 0.5 eq. of the one or more polymerizable compounds of the formula (XXIII) are reacted based on the total number of carboxylic acid groups of the polyacidic polymer having repeating units of formula (XXI).

The reaction conditions of the process are not particularly limited. Accordingly, it is possible to carry out the reaction in any suitable solvent or a suitable mixture of two or more solvents. Preferably, a solvent may be selected from the group of dimethylformamide (DMF), acetonitrile, carbon tetrachloride, tetrahydrofurane (THF), and dioxane. More preferably, dimethylformamide (DMF), acetonitrile, and/or carbon tetrachloride are used.

The reaction temperature is not particularly limited. Preferably, the reaction is carried out at a temperature of between −10° C. to the boiling point of the solvent. Preferably, the reaction temperature is in the range of from 0° C. to 100° C. The reaction time is not particularly limited. Preferably, the reaction time is in the range of from 10 minutes to 120 hours, more preferably 1 hour to 80 hours. The reaction between the polyacidic polymer (d) having repeating units of the following formula (XXI) and the one or more polymerizable compound of the formula (XXIII) may preferably be carried out at a temperature of from 20 to 100° C. for 1 to 60 hours.

The reaction product of the process may be isolated by precipitation and filtration. The product may be purified by washing with a suitable solvent.

Most preferably, the polyacidic polymer (d) has repeating units of the following formula (XXII')

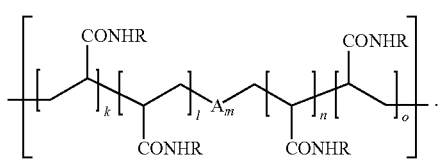
(XXII')

In formula (XXI'), R is as defined above for formula (XXII), k, l, m, n, and o are independently integers of at least 0, k+l+m+n+o is at least 2; at least one of k, l, n, and o is at least 1, and m is at least 1. Furthermore, A°, which may be the same or different, independently represent a group selected from groups of the following formula (XXII'c), (XXII'd), and (XXII'f):

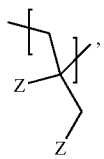
(XXII'c)

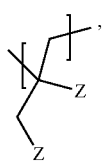
(XXII'd)

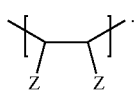
(XXII'f)

In formula (XXII'c), (XXII'd) and (XXII'f), Z is COOH or CONHR', wherein at least one Z is COOH, and R' is as defined above for formula (XXI).

Preferably, the polyacidic polymer having repeating units of formula (IV) has a weight average molecular weight of 1.2 to 400 kDa, more preferably 6 to 350 kDa, most preferably 12 to 300 kDa.

When the polyacidic polymer (d) has a weight-average molecular weight of less than 1 kDa, the strength of the cured dental composition is lowered. On the other hand, when the polyacidic polymer (d) has a weight-average molecular weight exceeding a viscosity of 400 kDa, upon mixing and blending the dental composition becomes harder, so that workability is lowered in some cases. Therefore, the preferred weight-average molecular weight of the polyacidic polymer (d) is from 1 to 300 kDa.

Further Optional Components

The dental composition according to the present invention may, besides of optional components reactive particulate filler (c) and polyacidic polymer (d), comprise additional optional components.

The dental composition according to the present invention may contain further components such as a redox initiator, further fillers besides of reactive particulate filler (a), components improving radio-opacity, solvents, free radical scavengers such as 4-methoxyphenol, polymerization inhibitors, surfactants (such as to enhance solubility of an inhibitor e.g., polyoxyethylene), coupling agents to enhance reactivity of fillers e.g. 3-(trimethoxysilyl) propyl methacrylate, and rheology modifiers.

Preferably, the dental composition contains a redox initiator.

The term "redox initiator" means a combination of an oxidizing agent and a reducing agent, and optionally a catalyst such as a metal salt. The redox initiator provides a redox reaction in which radicals are formed. These radicals initiate polymerisation of a radically polymerizable compound. Typically, a redox initiator system is activated by bringing the redox initiator system in contact with water and/or an organic solvent providing for at least partial dissolution of the oxidising agent and the reducing agent. The optional catalyst may be added to accelerate the redox reaction and thus the polymerization of the compound having a polymerizable double bond (a).

A mixture of the photoinitiator system (b) and a redox initiator is a "dual cure initiator system".

A suitable redox initiator system comprises reducing and oxidizing agents, which produce free-radicals capable of initiating polymerization of the polymerizable double bonds of the compound having a polymerizable double bond (a), independent from the presence of light. The reducing and oxidizing agents are selected such that the dental composition is sufficiently storage-stable and free of undesirable colorization to permit storage and use under typical dental conditions. Moreover, the reducing and oxidizing agents are selected so that the dual cure initiators system is sufficiently miscible with the resin system to permit dissolution of the redox initiator system in the composition.

Useful reducing agents include ascorbic acid, ascorbic acid derivatives, and metal complexed ascorbic acid compounds as described in U.S. Pat. No. 5,501,727; amines, namely tertiary amines, preferably tertiary aromatic amines such as 4-tert-butyl dimethylaniline; aromatic sulfinate salts such as p-toluenesulfinate salts and benzenesulfinate salts, most preferably sodium para-toluenesulfinate; thioureas, such as 1-ethyl-2-thiourea, tetraethyl thiourea, tetramethyl thiourea, 1,1-dibutyl thiourea, and 1,3-dibutyl thiourea; and mixtures thereof.

Other secondary reducing agents may include cobalt (III) chloride, ferrous chloride, ferrous sulfate, hydrazine, hydroxylamine, salts of a dithionite or sulfite anion, and mixtures thereof.

Suitable oxidizing agents include persulfuric acid and salts thereof, such as ammonium, sodium, potassium, cesium, and alkyl ammonium salts, preferably inorganic peroxodisulfate salts, most preferably potassium peroxodisulphate. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof. One or more different oxidizing agents or one or more different reducing agent may be used in the initiator system. Small quantities of transition metal compounds may also be added to accelerate the rate of redox cure. The reducing and oxidizing agents are present in amounts sufficient to permit an adequate free-radical reaction rate.

The reducing or oxidizing agents may be microencapsulated for enhancing shelf stability of the composition, and if necessary permitting packaging the reducing and oxidizing agents together (U.S. Pat. No. 5,154,762). Appropriate selection of an encapsulant may allow combination of the oxidizing and reducing agents and even of an acid-functional component and optional filler in a storage-stable state. Moreover, appropriate selection of a water-insoluble encapsulant allows combination of the reducing and oxidizing agents with the particulate reactive glass and water in a storage-stable state.

A particularly preferred redox initiator contains (i) an inorganic peroxodisulphate salt, (ii) an aromatic amine, and (iii) an aromatic or non-aromatic sulfinate salt. For the particularly preferred redox initiator, it is preferred that the inorganic peroxodisulphate salt is potassium peroxodisulphate; and/or the aromatic amine is tert.-butyl-N,N-dimethylaniline (4-tert.-butyl-N,N-dimethylaniline); and/or the aromatic sulfinate salt is sodium para-toluenesulfinate. Most preferably, the redox initiator contains (i') potassium peroxodisulphate, (ii') 4-tert.-butyl-N,N-dimethylaniline, and (iii') sodium para-toluenesulfinate.

Preferably, a dual cure initiator system contains the photoinitiator system with the covalently bonded coinitiator compound having formula (I) or (II), and the redox initiator contains (i) an inorganic peroxodisulphate salt, (ii) an aromatic amine, and (iii) an aromatic or non-aromatic sulfinate salt, more preferably the redox initiator contains (i') potassium peroxodisulphate, (ii') tert.-butyl-N,N-dimethylaniline, and (iii') sodium para-toluenesulfinate.

Further filler(s) besides of the reactive particulate filler (c) may for example be selected from inert glass(es), fluoride releasing glass(es), granulated prepolymerized fillers, ground prepolymerized fillers and filler aggregates.

The term "inert glass(es)" refers to a glass which is not capable of reacting with a polymer containing acidic groups in a cement reaction. Inert glasses are for example described in the Journal of Dental Research June 1979, pages 1607-1619, or more recently in U.S. Pat. Nos. 4,814,362, 5,318, 929, 5,360,770, and application US 2004/0079258 A1. Specifically, from US 2004/0079258 A1, inert glasses are known in which strongly basic oxides such as CaO, BaO, SrO, MgO, ZnO, $Na_2O$, $K_2O$, $Li_2O$ etc. are replaced with weakly basic oxides such as those in the Scandium or Lanthanide series.

The term "fluoride releasing glass(es)" refers to a glass capable of to of releasing fluoride. Fluoride releasing capability may be provided by adding to a mixture of oxides for forming a glass inorganic particles containing fluoride with the proviso that the glass has fluoride releasability, preferably sustained fluoride releasability. Such inorganic particles may be selected from the group consisting of sodium fluoride, strontium fluoride, lanthanum fluoride, ytterbium fluoride, yttrium fluoride, and calcium-containing fluoroaluminosilicate glasses.

Components improving radio-opacity may for example be selected from $CaWO_4$, $ZrO_2$ and $YF_3$.

Suitable solvents may be selected from water, alcohols such as methanol, ethanol, propanol (n-, i-), butanol (n-, iso-, tert.-), and ketones such as acetone.

The dental composition of the present invention may preferably comprise a solvent in an amount of 5 to 75 percent by weight based on the total weight of the dental composition.

Preferably, in the dental composition of the present invention, water is present in an amount from about 0.5 wt % to about 40 wt %, more preferably 1.0 wt % to 30 wt %, most preferably 2.0 wt % to 25 wt % based on the total weight of the dental composition. This preferred amount of water is particularly suitable for a dental composition in the form of a dental glass ionomer cement, that is a dental composition comprising the reactive particulate filler (c) and the polyacidic polymer (d).

One-Pack or Multi-Pack Dental Composition

The present dental composition may be a one-pack or a multi-pack dental composition.

The term "one-pack" as used herein means that all components of the dental composition are comprised in one single pack such as a capsule having at least two chambers.

The term "multi-pack" as used herein means that the components of the dental composition are comprised in a multitude of separate packs. For example, a first part of components is comprised in a first pack, while as second part of components is comprised in a second pack, a third part of components may be comprised in a third pack, a fourth part of components may be comprised in a fourth pack, and so on.

Preferably, the dental composition is a composition of two or more packs, more preferably a two-pack composition. For a two-pack dental composition, a two-pack powder/liquid composition is preferred.

Preferably, in a two-pack powder/liquid composition, the powder pack comprises the particulate carrier (b2) and optionally the reactive particulate filler (c), and the liquid pack comprises the compound having a polymerizable double bond (a) and optionally the polyacidic polymer (d).

Use of a Particulate Carrier

A particulate carrier displaying multiple covalently bonded tertiary amino groups and/or tertiary phosphine groups on the surface, may be used in a dental composition for crosslinking polymer chains formed by polymerizing a compound having a polymerizable double bond.

Preferably, the above described particulate carrier is the particulate carrier (b2) described above for the dental composition. Furthermore, preferably, in the use of the particulate carrier, the dental composition is a dental composition as described above.

The invention will now be further illustrated by the following Examples.

EXAMPLES

Example 1

Synthesis of 4-(dimethylamino)-N-[3-(triethoxysilyl)propyl] benzamide (SAR 1-155-1)

To a solution of 3.47 g (19 mmol) 3-Aminopropyltrimethoxysilane in 100 mL Dichloromethane were added dropwise 2.16 g (21 mmol) triethylamine at 0-5° C. Thereafter, a suspension of 4.0 g (22 mmol) Dimethylamino benzoyl chloride in 40 ml Dichloromethane was dropped to the first solution under ice cooling and stirred for 1 hour under cooling. Then the reaction mixture was stirred overnight and the precipitated product was filtered off and dried.

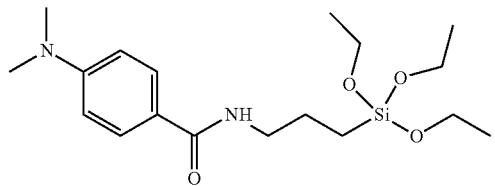 [SMILES: CCO[Si](CCCNC(=O)c1ccc(N(C)C)cc1)(OCC)OCC]

$C_{18}H_{32}N_2O_4Si$, $M_n$=368.55 g/mol $^{13}C$ NMR (DMSO-$d_6$): δ (ppm)=167.67 (CONH), 152.92 (Ar—N($CH_3)_2$), 130.82 (Ar—NH), 118 (Ar), 110.70 (Ar), 45.45 (NH—$CH_2$), 39.9 (N$CH_3$), 22.2 ($CH_2\underline{CH_2}CH_2$), 10.16 ($CH_3$)

Condensation of 4-(dimethylamino)-N-[3-(triethoxysilyl)propyl] benzamide to Nanocondensate 1

The raw product was dispersed in 50 mL water in an ultrasound bath. After 1 hour 0.8 g Ammonium fluoride was added and treated for another hour in the ultrasound bath. Then, the Water was removed in vacuum and the product was dried at 50° C. and 50 mbar.

Yield: 5.41 (87%)

Example 2

Condensation of 3-Aminopropyl triethoxysilane onto Glass Filler (REN 1-104-1)

10.2 g Aerosil OX-50 was dispersed in 100.2 g isopropanol. 0.24 g (3-Aminopropyl) trimethoxy silane were added and the mixture was stirred at 50° C. for 5 minutes. Solvent was evaporated at 125 mbar and 50° C. by rotary evaporation. Afterward the powder was dried at 80° C. overnight.

Reaction to 4-(dimethylamino)-N-[3-(triethoxysllyl)propyl] benzamide Modified Aeorsil (JBR 3-147-1)

A solution of 0,371 g 4-(dimethylamino) Benzoyl chloride in 80 ml ice cooled Dichloromethane was added to a suspension of 7.42 g of 3-Aminopropyl triethoxysilane modified Aerosil (REN 1-104-1) and triethylamine in 100 ml Dichloromethane, stirred for 3 h at 4° C. and additional stirred overnight at room temperature. The supernatant solution was decanted, washed twice with 50 ml DCM and dried in a vacuum oven.

Yield: 4.23 g of a white powder

Application Example 1

Liquid
In 10 g ethoxylated Bisphenol A dimethacrylate were dissolved homogeniously 0.05 g camphorquinone.

Powder
To 20 g of a barium-alumosilicate glass (TPH$^3$ Spectrum Glass) were added 1.5 g of Nanocondensate 1 and homogenized by tumbling for 30 min.

15 g of the powder and 5 g of the liquid prepared as described above were put in a Speedmixer MA-QC-165 (60 ml cup) using the following mixing procedure: two times mixing speed 1500 rpm and time 3 min, finally, mixing speed 1000 rpm, time 3 min and vacuum 100 mbar.

The obtained composite was irradiated with a SmartLite Focus for 20 s resulting in a hard polymerized composite material.

Application Example 2

Liquid
In 10 g ethoxylated Bisphenol A dimethacrylate were dissolved homogeneously 0.05 g camphorquinone.

Powder
To 20 g of a barium-alumosilicate glass (TPH$^3$ Spectrum Glass) were added 1.5 g of 4-(dimethylamino)-N-[3-(triethoxysilyl)propyl] benzamide modified Aerosil (JBR 3-147-1) and homogenized by tumbling for 30 min.

15 g of the powder and 5 g of the liquid prepared as described above were put in a Speedmixer MA-QC-165 (60 ml cup) using the following mixing procedure: two times mixing speed 1500 rpm and time 3 min, finally, mixing speed 1000 rpm, time 3 min and vacuum 100 mbar.

The obtained composite was irradiated with a SmartLite Focus for 20 s resulting in a hard polymerized composite material.

The invention claimed is:

1. A dental composition comprising
   (a) a compound having a polymerizable double bond,
   (b) a photoinitiator system comprising
      (b1) a photosensitizer absorbing light in the range of from 400 to 800 nm, and
      (b2) a particulate carrier supporting a coinitiator covalently bonded to the surface of the carrier, wherein the particulate carrier displays multiple covalently bonded tertiary amino groups and/or tertiary phosphine groups on the surface, for crosslinking monomers, oligomers and/or polymers having one or more polymerizable double bonds, wherein the particulate carrier is a polycondensate of a particulate oxide treated with a silane treatment agent having the multiple covalently bonded tertiary amino groups and/or tertiary phosphine groups, the particulate oxide being formed from a mixture of a silica precursor component and optionally one or more compounds selected from compounds of aluminum, zinc, titanium, zirconium, tungsten, ytterbium, hafnium, bismuth, barium, strontium, silver, tantalum, lanthanum, tin, boron, and cerium, the particulate oxide having an average particle size of from 1 to 50 nm.

2. The dental composition according to claim 1, wherein the particulate carrier is a nanoparticle.

3. The dental composition according to claim 1, wherein the photosensitizer is a 1,2-diketone compound.

4. The dental composition according to claim 1, wherein the particulate carrier is a nanoparticle comprising alumina, zirconia, titania, or a mixture thereof.

5. The dental composition according to claim 4, wherein the nanoparticle has an average particle size of from 1 to 50 nm.

6. The dental composition according to claim 2, wherein the nanoparticle has a density of covalently bonded tertiary amino groups and/or tertiary phosphine group of from 0.1 to 100 groups per nm$^2$.

7. The dental composition according to claim 2, wherein the polycondensate is obtainable by
   (i) hydrolysing the mixture containing
      (A) the silica precursor component, and optionally
      (B) the one or more compounds selected from compounds of aluminum, zinc, titanium, zirconium, tungsten, ytterbium, hafnium, bismuth, barium, strontium, silver, tantalum, lanthanum, tin, boron, and cerium;
   (ii) converting the silica precursor component (A) and the optionally compounds (B) into a particulate oxide having an average particle size of from 1 to 50 nm;
   (iii) treating the particulate oxide with the silane treatment agent having one or more covalently bonded tertiary amino groups or tertiary phosphine groups for obtaining the polycondensate displaying multiple covalently bonded tertiary amino groups or tertiary phosphine groups on the surface.

8. The dental composition according to claim 1, wherein the covalently bonded tertiary amino groups and/or tertiary phosphine groups are selected from moieties of the following formulae (I) and (II):

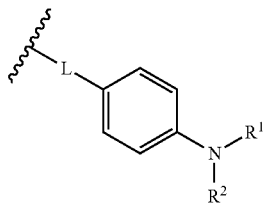

(I)

wherein
$R_1$ and $R_2$
which may be the same or different, independently represent a $C_{1-6}$ straight-chain, $C_3$ branched or cyclic alkyl group; and

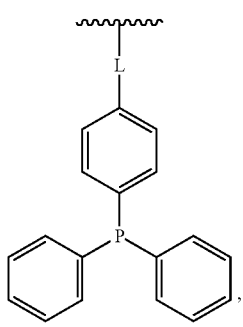

(II)

and L is a single bond or a divalent linker group.

9. The dental composition according to claim 8, wherein in formula (I) or (II), L is a divalent linker group of formula (III)

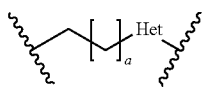

(III)

wherein a is 0 or an integer of from 1 to 10, and Het is selected from the group of sulfur, oxygen, and a nitrogen atom substituted with a hydrogen atom or a straight-chain $C_{1-6}$ alkyl group or a branched or cyclic $C_{3-6}$ alkyl group.

10. The dental composition according to claim 1, which is selected from dental glass ionomer cement, a dental cement, a dental adhesive composition, a dental bonding agent, a dental primer, a dental infiltrant, a pit and fissure sealant, a dental desensitizing composition, a pulp capping composition, a dental composite, and a sealing and protecting composition for naked tooth necks.

11. The dental composition according to claim 10, which is a dental composition further comprising
    (c) a reactive particulate filler, and
    (d) a polyacidic polymer which is reactive with the reactive particulate filler in a cement reaction.

12. The dental composition according to claim 11, wherein (a) the compound having a polymerizable double bond is selected from
    (a1) a water-soluble, hydrolysis-stable monomer having a single polymerizable double bond and optionally a carboxylic acid group or hydroxyl group; and
    (a2) a water-soluble, hydrolysis-stable polymerizable crosslinker having at least two polymerizable carbon-carbon double bonds.

13. The dental composition according to claim 1, wherein the mixture comprises the one or more compounds selected from compounds of aluminum, zinc, titanium, zirconium, tungsten, ytterbium, hafnium, bismuth, barium, strontium, silver, tantalum, lanthanum, tin, boron, and cerium.

14. The dental composition according to claim 1, wherein the particulate carrier displays multiple covalently bonded tertiary phosphine groups on the surface.

* * * * *